(12) United States Patent
Powis et al.

(10) Patent No.: US 8,124,651 B2
(45) Date of Patent: Feb. 28, 2012

(54) PALMARUMYCIN BASED INHIBITORS OF THIOREDOXIN AND METHODS OF USING SAME

(75) Inventors: Garth Powis, Houston, TX (US); Peter Wipf, Pittsburg, PA (US)

(73) Assignees: The University of Pittsburgh Office of Technology Transfer, Pittsburgh, PA (US); Arizona Board of Regents, Tucson, AZ (US)

( * ) Notice: Subject to any disclaimer, the term of this patent is extended or adjusted under 35 U.S.C. 154(b) by 637 days.

(21) Appl. No.: 12/066,426

(22) PCT Filed: Sep. 15, 2006

(86) PCT No.: PCT/US2006/036295
§ 371 (c)(1),
(2), (4) Date: Oct. 7, 2008

(87) PCT Pub. No.: WO2007/035641
PCT Pub. Date: Mar. 29, 2007

(65) Prior Publication Data
US 2009/0131511 A1 May 21, 2009

Related U.S. Application Data

(60) Provisional application No. 60/717,398, filed on Sep. 15, 2005.

(51) Int. Cl.
*A61K 31/357* (2006.01)
*C07D 319/08* (2006.01)

(52) U.S. Cl. .......................... 514/452; 549/358; 549/359

(58) Field of Classification Search ........................ None
See application file for complete search history.

(56) References Cited

U.S. PATENT DOCUMENTS
6,673,937 B2   1/2004   Lazo et al.

FOREIGN PATENT DOCUMENTS
WO   WO 2007/035641 A2   3/2007

OTHER PUBLICATIONS

Wipf et al., "Synthesis of Highly Oxygenated Dinaphthyl Ethers via SNAr Reactions Promoted by Barton's Base" Organic Letters (2003) vol. 5 No. 7 pp. 1155-1158.*
Coutts et al., "Novel synthetic approaches to the palmarumycin skeleton" Tetrahedron Letters (2000) vol. 41 pp. 9105-9107.*
The Merck Manual of Diagnosis and Therapy, seventeenth edition, 1999, Published by Merck Research Laboratories, pp. 397-398, 948-949, 1916, and 1979-1981.*
The Oxford Textbook of Oncology, 1995, published by Oxford University Press, pp. 447-453.*
Wipf et al., "Synthesis and biological activity of prodrug inhibitors of the thioredoxin-thioredoxin reductase system" Organic and Biomolecular Chemistry (2005) vol. 3 pp. 3880-3882.*
Gorreta et al., "Identification of Thioredoxin Reductase 1-Regulated Genes Using Small Interference RNA and cDNA Microarray" Cancer Biology and Therapy (2005) vol. 4 No. 10 pp. 1079-1088.*
Mukherjee et al., "The thioredoxin system: a key target in tumour and endothelial cells" The British Journal of Radiology (2008) vol. 81 pp. S67-S68.*
Gan et al., "Inhibitory Effects of Thioredoxin Reductase Antisense RNA on the Growth of Human Hepatocellular Carcinoma Cells" Journal of Cellular Biochemistry (2005) vol. 96 pp. 653-664.*
Smart et al., "Thioredoxin Reductase as a Potential Molecular Target for Anticancer Agents That Induce Oxidative Stress" Cancer Research (2004) vol. 64 pp. 6716-6724.*
Hopkins, Studies in Natural Product Chemistry: Synthesis of Palmarumycin CP1 Analogs and Total Synthesis and Structure Validation of (+) Bistramide C (etd08232005-23211) Doctoral Dissertation, defended Aug. 1, 2005. University of Pittsburgh (Retrieved Mar. 25, 2007 at URL http://etd.library.pitt.edu/ETD/available/etd-08232005-230211/); p. 43, Fig. 18.
Baker et al, Thioredoxin Gene, a Gene Found Overexpressed in Human Cancer, Inhibits Apoptosis in Vitro and in Vivo, 1997, Cancer Research 57(220):5162-6168.
Kunkel et al., Cell Line-Directed Screening Assay for Inhibitors of Thioredoxin Reductase Signaling as Potential Anti-Cancer Drugs, 1997, Anti-Cancer Drug Design 12(8):659-670.
Wipf et al., Natural Product Based Inhibitors Thioredoxin-Thioredoxin Reductase System 2004, Org. Biol. Chem. 2(11): 1651-1658.
Gennaro, Remington's Pharmaceutical Sciences, 18th ed., Mack Publishing, Easton, PA 1990 (TOC).

* cited by examiner

*Primary Examiner* — Eric S Olson
(74) *Attorney, Agent, or Firm* — Stephen A. Bent; Foley & Lardner LLP

(57) ABSTRACT

Embodiments of the present invention relate to inhibitors of thioredoxin. Certain embodiments relate to palmarumycin based compounds and methods of using the same. Such compounds may be useful in inhibiting the overexpression of thioredoxin, inhibiting tumor growth and treating cancer.

16 Claims, 8 Drawing Sheets

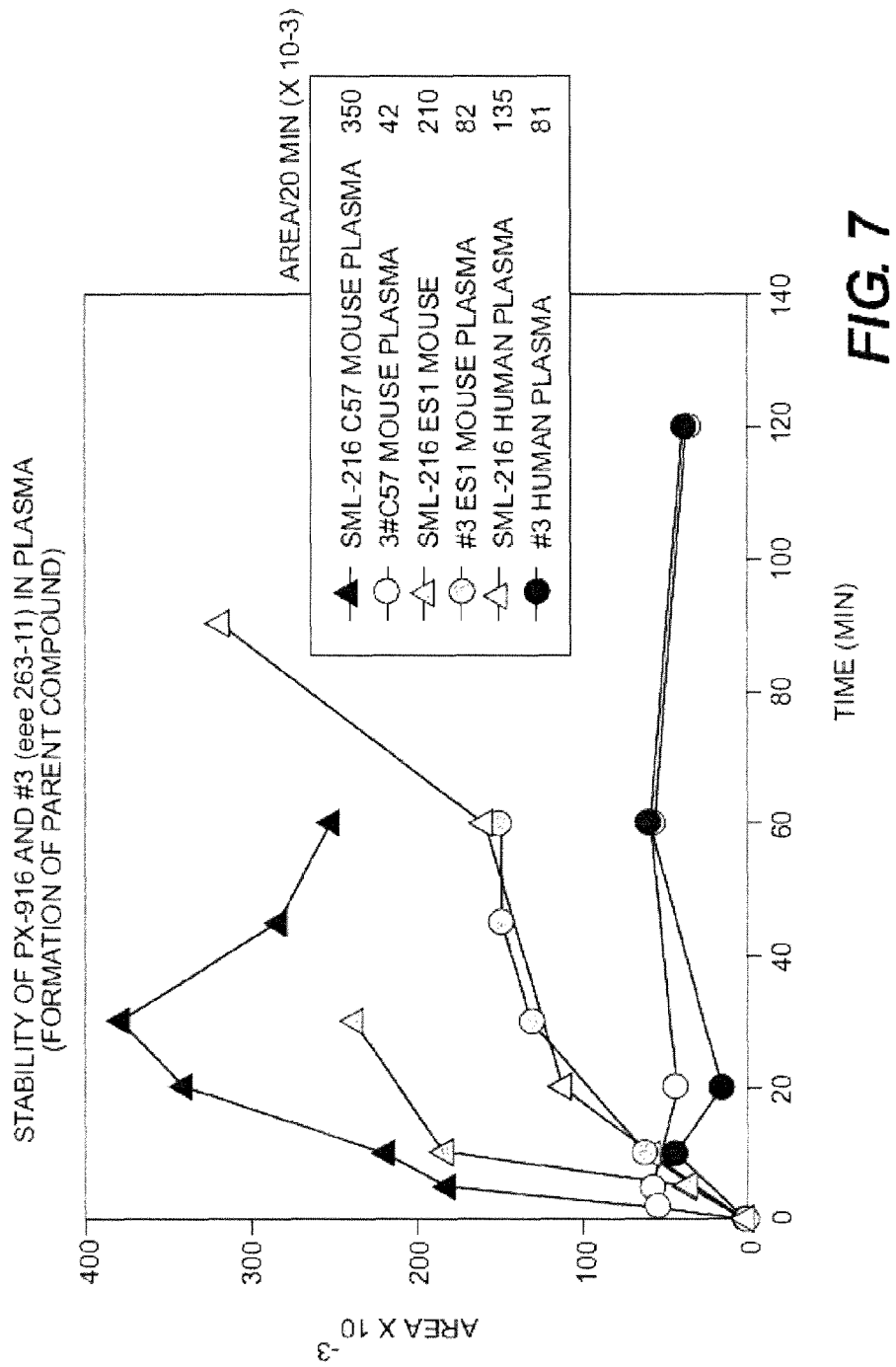

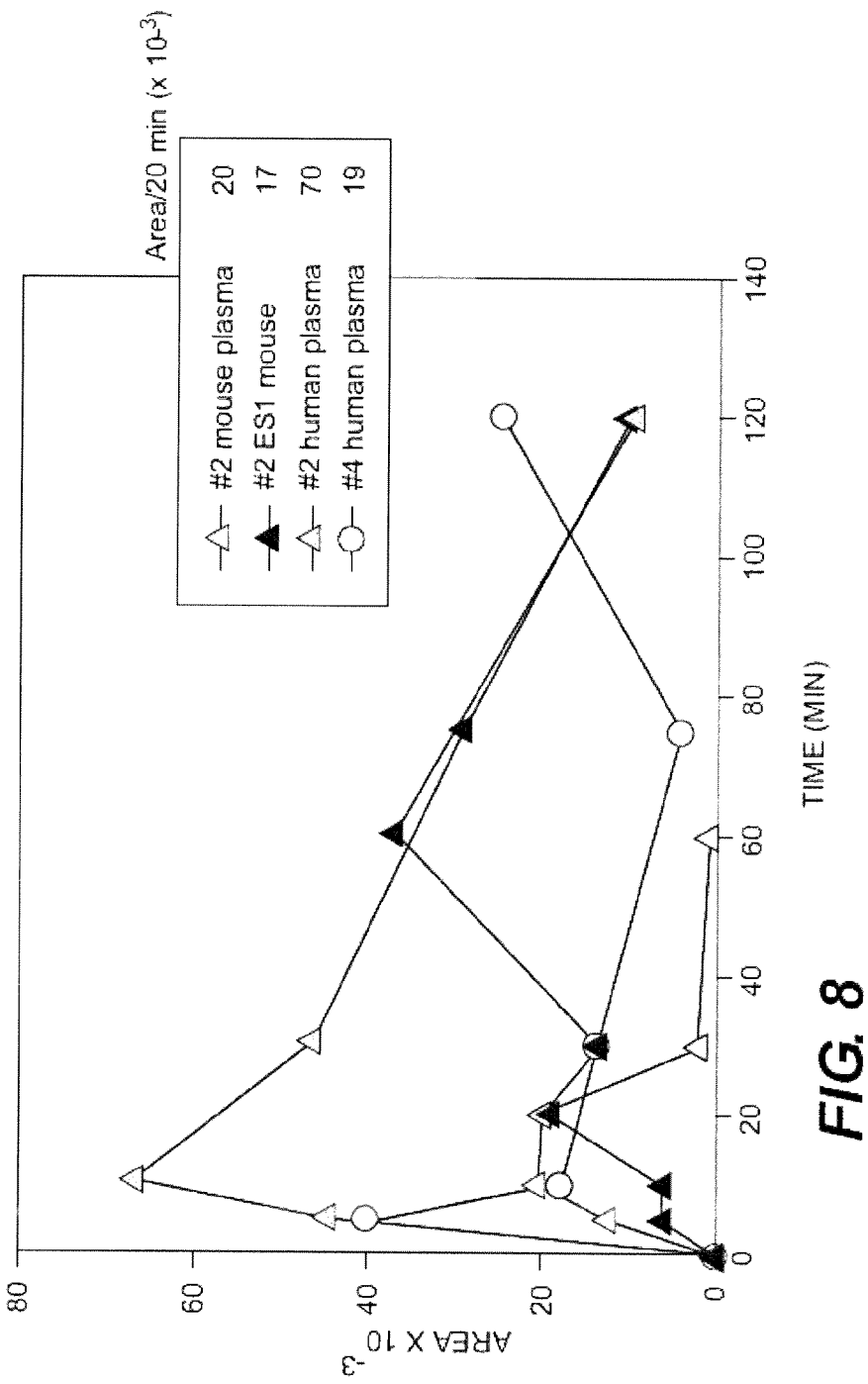

PALMARUMYCIN BASED INHIBITORS OF THIOREDOXIN AND METHODS OF USING SAME

This application claims priority to U.S. Provisional Application No. 60/717,398 filed Sep. 15, 2005 titled "PALMARUMYCIN BASED COMPOUNDS AND METHODS OF USING SAME" with the United States Patent and Trademark Office, the contents of which are incorporated herein by reference.

GOVERNMENT INTERESTS

This invention was made with government support under U19 CA052995 awarded by the National Institutes of Health. The government has certain rights in the invention.

BACKGROUND

The thioredoxin redox couple thioredoxin/thioredoxin reductase (TR/Trx) is a ubiquitous redox system found in both prokaryotic and eukaryotic cells. The thioredoxin system is comprised primarily of two elements: thioredoxin and thioredoxin reductase. Thioredoxins are a class of low molecular weight redox proteins characterized by a highly conserved Cys-Gly-Pro-Cys-Lys active site. The cysteine residues at the active site of thioredoxin undergo reversible oxidation-reduction catalyzed by thioredoxin reductase. Trx-1 is ubiquitously expressed with a conserved catalytic site that undergoes reversible NADPH-dependent reduction by selenocysteine-containing flavoprotein Trx-1 reductases.

The cytosolic thioredoxin redox system is composed of thioredoxin-1 and thioredoxin reductase-1 reductase, which catalyzes the NADPH-dependent reduction of thioredoxin-1. Thioredoxin reductase-1 is an important regulator of cancer cell growth and survival. Thioredoxin-1 acting with peroxiredoxin-1 is an antioxidant that scavenges $H_2O_2$. Thioredoxins are also able to reduce buried oxidized thiol residues in proteins and regulate the activity of redox-sensitive transcription factors, including p53, nuclear factor-nB, the glucocorticoid receptor, activator protein-1, hypoxia-inducible factor-1 (HIF-1), Sp1, and Nrf2. Thioredoxin-1 also binds and inhibits the activity of the apoptosis inducing proteins, apoptosis signal-regulating kinase-1 and, the tumor suppressor phosphatase and tensin homologue deleted on chromosome 10, thus inhibiting apoptosis. Thioredoxin-1 is overexpressed in many human tumors where it is associated with increased cell proliferation, decreased apoptosis, and poor patient survival. Thioredoxin reductase thus provides a target to regulate the activity of overexpressed thioredoxin-1.

Thioredoxin reductase-1 is a selenocysteine-containing flavoprotein with broad substrate specificity because of the ready accessibility of its COOH-terminal redox active site, which contains an essential selenocysteine residue. There are three thioredoxin reductase isoforms: the canonical cytoplasmic thioredoxin reductase-1, a mitochondrial thioredoxin reductase-2, and a testes-specific thioredoxin reductase/glutathione reductase. The cellular level of thioredoxin reductase-1 is subject to complex regulation. The core promoter of the thioredoxin reductase-1 gene contains several transcription factor activation sites, including those for the redox-sensitive factors Oct-1 and Sp1 as well as others. Differential splicing and alternative transcription start sites result in multiple forms of the enzyme. Post-transcriptional regulation involving a selenocysteine insertion sequence element in the 3V-untranslated region directs selenocysteine incorporation, which is necessary for enzyme activity; thus, selenium supplementation can lead to increased thioredoxin reductase-1 activity in cell culture and in selenium deficient animals. Thioredoxin reductase-1 is necessary for cell proliferation. A thioredoxin reductase-1 knockout is embryonic lethal in mice, and thioredoxin reductase-1-deficient fibroblasts derived from the thioredoxin reductase-1 (−/−) embryos do not proliferate in vitro. Furthermore, cancer cell growth is inhibited by thioredoxin reductase-1 antisense, thioredoxin reductase-1 small interfering RNA and by a mutant redox inactive thioredoxin reductase-1. There are reports that levels of thioredoxin reductase-1 are increased by epidermal growth factor and hypoxia in cancer cells, although tumors show only moderately increased levels of thioredoxin reductase-1.

The redox protein thioredoxin-1 (Trx-1) has been proven to be a rational target for anticancer therapy involved in promoting both proliferation and angiogenesis, inhibiting apoptosis, and conferring chemotherapeutic drug resistance. Trx-1 was originally studied for its ability to act as a reducing cofactor for ribonucleotide reductase, the first unique step in DNA synthesis. Thioredoxin also exerts specific redox control over a number of transcription factors to modulate their DNA binding and, thus, to regulate gene transcription. Transcription factors regulated by thioredoxin include, but are not limited to, NF-κβ, p53, TFIIIC, BZLF1, the glucocorticoid receptor, and hypoxia inducible factor 1α (HIF-1α). Trx-1 also binds in a redox-dependent manner and regulates the activity of enzymes such as apoptosis signal-regulating kinase-1 protein kinases C δ, є, ξ, and the tumor suppressor phosphatase PTEN. Trx-1 expression is increased in several human primary cancers, including, but not limited to, lung, colon, cervix, liver, pancreatic, colorectal, and squamous cell cancer. Clinically increased Trx-1 levels have been linked to aggressive tumor growth, inhibition of apoptosis, and decreased patient survival.

Regulation of the thioredoxin-thioredoxin reductase (Trx-1/TrxR) system is attracting increasing interest due to its implication in cancer, HIV-AIDS and rheumatoid arthritis along with other medical conditions. The naphthoquinone spiroketal pharmacophore of the palmarumycin family of fungal metabolites holds promising biological activity against the Trx-1/TrxR system. Embodiments of the present invention relate to various analogues of the palmarumycin family and the ability of these analogues to inhibit the thioredoxin-thioreductase system.

SUMMARY OF THE INVENTION

Aspects of the present invention generally relate to analogs of palmarumycin. Such analogs may be effective in inhibiting thioredoxin/thioredoxin reductase (Trx/TrxR) system. Inhibition of the TrxTrxR system may lead to inhibition of tumor growth. Therefore, further embodiments of the present invention provide compounds and pharmaceutical compositions for the inhibition of tumor growth.

Embodiments of the invention provide analogs of palmarumycin which can serve as lead compounds for the identification of a more efficacious inhibitory compound. Further embodiments include use of the O-glycyl naphthoquinone spiroketal derivative of the palmarumycin as a lead compound for the further development of Trx/TrxR system inhibitory compounds. Embodiments of the invention also contemplate providing a palmarumycin derivative that may be cleaved to an active compound under physiological conditions.

Embodiments of the invention also provide methods of inhibiting the Trx/TrxR system. Inhibition of the Trx/TrxR system may further inhibit various transcription factors, and subsequently promote apoptosis. Thus, further embodiments provide methods of inhibiting tumor growth in a subject in need of such treatment.

Embodiments of the invention relate to a compound, or salt thereof, having the general formula:

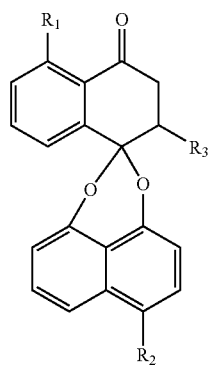

wherein $R_1$ may be H or OH;

$R_2$ may be OH, $OCH_3$, $O(CH_2)nCH_3$, $OCH(CH_3)CH_2nCH_3$, wherein n is 1-4, $OCH_2CH_2$-morpholino, $OC(O)CH_2NH_2$, $OC(O)CH(CH_3)NH_2$, $OC(O)CH(CH(CH_3)_2)NH_2$, $OC(O)CH(CH_2Phenyl)NH_2$, $OC(O)CH(CH_2\ p\text{-}OHPhenyl)NH_2$

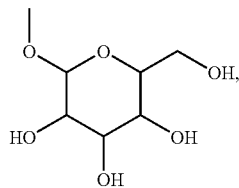

$OC(O)CH(CH_2OH)NH_2$, $OC(O)CH(CH_2SH)NH_2$, $OC(O)CH(CH_2COOH)NH_2$, $OC(O)CH(CH_2CH_2COOH)NH_2$, $OC(O)CH(CH_2CONH_2)NH_2$, $OC(O)CH(CH_2CH_2CONH_2)NH_2$, $OC(O)CH(CH(CH_3)CH_2CH_3)NH_2$, $OC(O)CH(CH_2CH(CH_3)_2)NH_2$, or $OC(O)CH(CH(OH)CH_3)NH_2$;

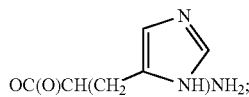

and $R_3$ may be a hydrogen, $NHNHC(CH_3)_2CONH_2$ or a carbon-carbon bond, with the proviso that if $R_1$ is OH and $R_3$ is a carbon-carbon bond, $R_2$ is not OH; or salts thereof. Exemplary salts include, but are not limited to HCl, TFA, tosylate or any other pharmaceutically acceptable salt.

In an alternative embodiment provided is a compound having the following structure:

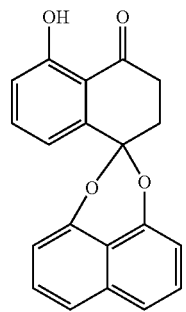

Palmarumycin CP1.

In another alternative embodiment provided is a compound having the following structure:

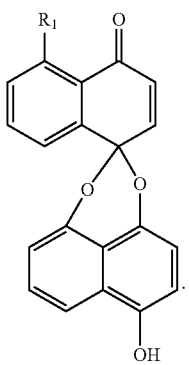

PX-960

Preferred embodiments relate to a compound of the structure:

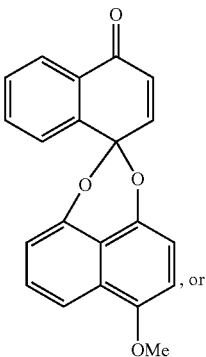

(PX-911)

-continued
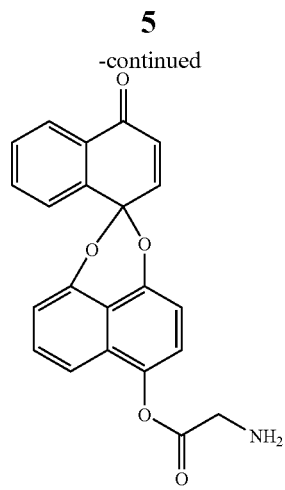
or salts thereof.
In a preferred embodiment, a salt of a palmarumycin compound has the structure:
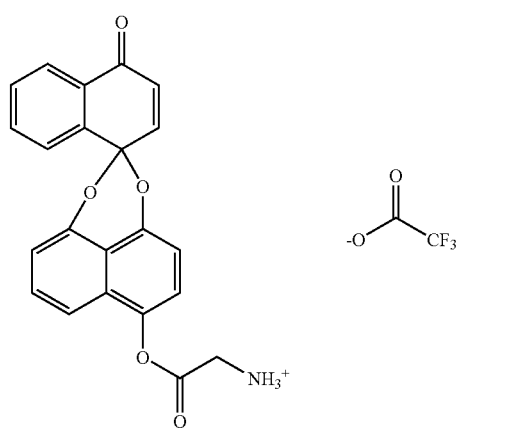
Other embodiments include compounds of the structures:
eee269-II
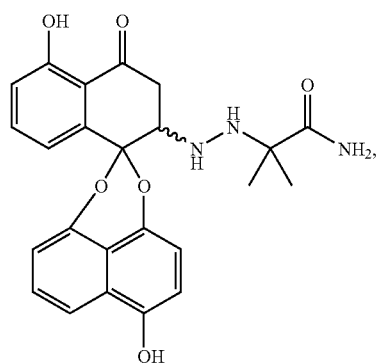
-continued
eee86-III
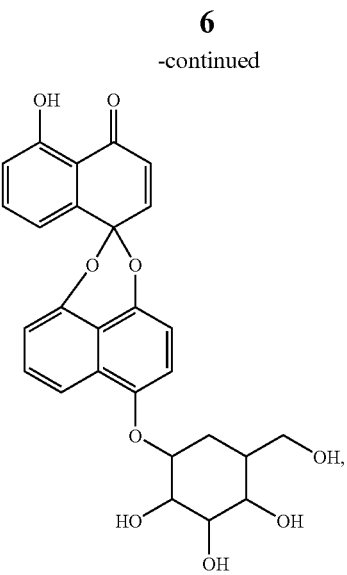
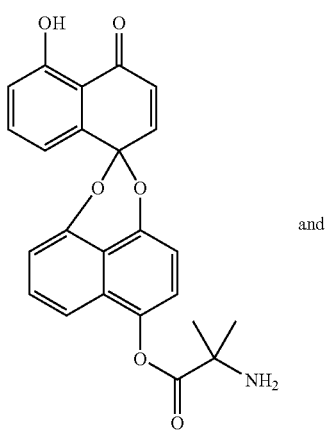
and
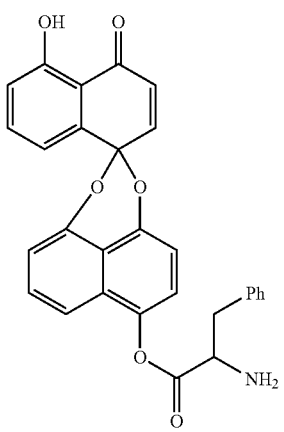
or salts thereof.

Preferred salts of the foregoing compounds include the following:

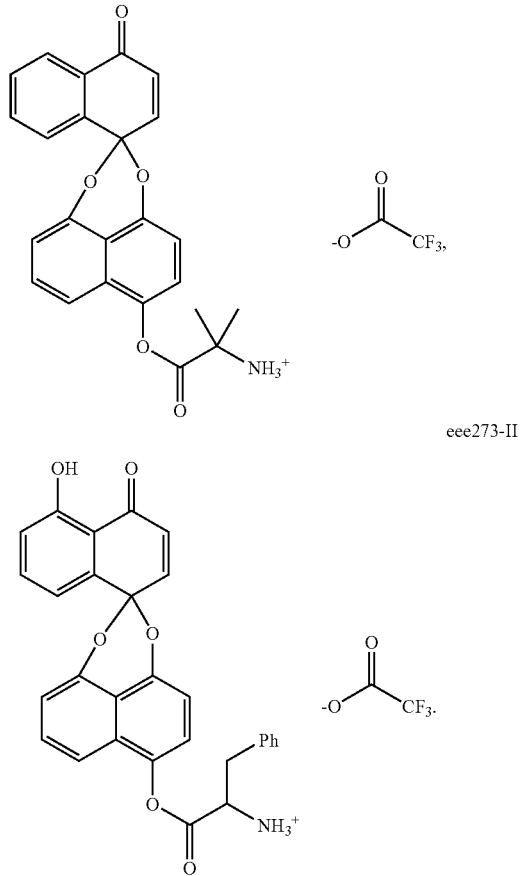

Embodiments further provide a compound derived from a palmarumycin wherein the compound inhibits a thioredoxin/thioredoxin reductase system. In one embodiment, the compound is a naphthoquinone spiroketal derivative. In another embodiment the compound is an O-glycyl naphthoquinone spiroketal derivative. Embodiments also provide an O-glycl naphthoquinone spiroketal derivative of palmarumycin.

Embodiments of the invention further provide a method of inhibiting a thioredoxin/thioredoxin reductase system comprising contacting a cell with a palmarumycin analog; and inhibiting the thioredoxin/thioredoxin reductase system. In one embodiment of the method, the palmarumycin analog is an O-glycyl naphthoquinone spiroketal derivative.

An embodiment of the present invention provides a method of inhibiting tumor growth comprising administering a therapeutically effective amount of a palmarumycin analog to inhibit tumor growth. In preferred embodiments, the palmarumycin analog may be an O-glycl naphthoquinone spiroketal derivative of palmarumycin. The O-glycyl naphthoquinone spiroketal derivative may also be cleaved in vivo to an active palmarumycin analog.

Another embodiment is a method for making a derivative of a palmarumycin comprising introducing a charged, hydrolytically cleavable function to a naphthoquinone spiroketal scaffold of palmarumycin to form a derivative of palmarumycin.

In a further embodiment, a method for making a compound that inhibits a thioredoxin/thioredoxin reductase system in vivo is provided. The method comprises identifying a compound as a lead compound, modifying the lead compound, and selecting at least one analog of the lead compound that exhibits inhibition of the thioredoxin/thioredoxin reductase system. The lead compound may be palmarumycin. In another embodiment, the lead compound may be an O-glycl naphthoquinone spiroketal derivative of the palmarumycin.

DESCRIPTION OF THE DRAWINGS

In part, other aspects, features, benefits and advantages of the embodiments of the present invention will be apparent with regard to the following description, appended claims and accompanying drawings where:

FIG. 7. Stability of PX-916 and eee 263-111 in plasma.
FIG. 8. Stability of eee 86-11 and eee273-11 in plasma.

DESCRIPTION OF THE INVENTION

Figure 1:
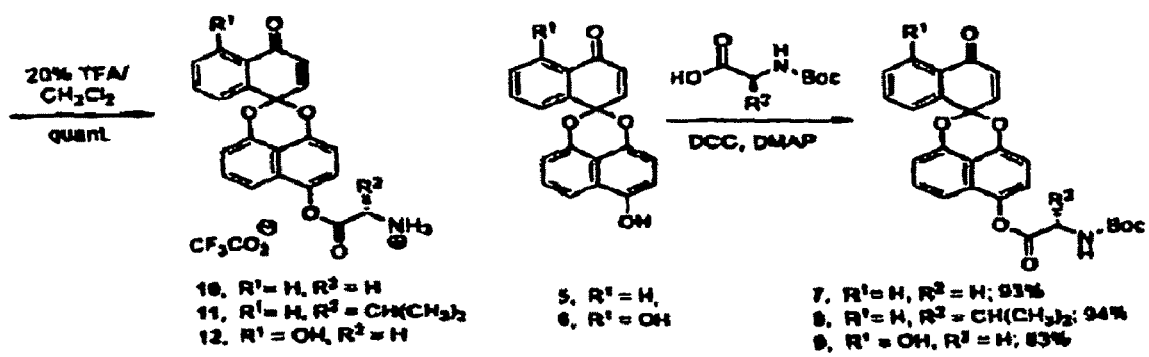
FIG. 1. Preparation of glycine and valine-derived prodrugs.

Embodiments of the invention relate to the generation of analogs of palmarumycin. Analogs are tested for their efficacy in inhibiting the thioredoxin/thioredoxin reductase system. Also, the analogs may be used as lead compounds to identify further lead compounds and/or compounds for therapeutic use. The ability of these analogs to inhibit the thioredoxin-thioredoxin reductase system, both in vitro and in vivo, may provide beneficial and useful therapeutic agents. Embodiments of the invention further relate to the anti-proliferative actions of the palmarumycin analogues in tumor cells.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. As used herein, the term "analog" or "derivative" are used interchangeably to mean a chemical substance that is related structurally and functionally to another substance. An analog or derivative contains a modified structure from the other substance, and maintains the function of the other substance, in this instance, inhibiting a thioredoxin/thioredoxin reductase. The analog or derivative need not, but can be synthesized from the other substance. For example, a palmarumycin analog means a compound structurally related to palmarumycin, but not necessarily made from palmarumycin.

Optical Isomers-Diastereomers-Geometric Isomers-Tautomers. Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The formulas are shown without a definitive stereochemistry at certain positions. The present invention includes all stereoisomers of such formulas and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general formula may be obtained by stereospecific synthesis using optically pure starting materials or reagents of known configuration.

As used herein, the term "about" means plus or minus 10% of the numerical value of the number with which it is being used. Therefore, about 50% means in the range of 45%-55%.

"Optional" or "optionally" means that the subsequently described event or circumstance may or may not occur, and that the description includes instances where the event occurs and instances where it does not.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal without the production of undesirable physiological effects such as nausea, dizziness, rash, or gastric upset. In a preferred embodiment, the therapeutic composition is not immunogenic when administered to a human patient for therapeutic purposes.

"Providing" when used in conjunction with a therapeutic means to administer a therapeutic directly into or onto a target tissue or to administer a therapeutic to a patient whereby the therapeutic positively impacts the tissue to which it is targeted.

As used herein "subject" or "patient" refers to an animal or mammal including, but not limited to, human, dog, cat, horse, cow, pig, sheep, goat, chicken, monkey, rabbit, rat, mouse, etc.

As used herein, the term "therapeutic" means an agent utilized to treat, combat, ameliorate, prevent or improve an unwanted condition or disease of a patient. The methods herein for use contemplate prophylactic use as well as curative use in therapy of an existing condition.

The terms "therapeutically effective" or "effective", as used herein, may be used interchangeably and refer to an amount of a therapeutic composition embodiments of the present invention. For example, a therapeutically effective amount of a composition comprising an analogue of palmarumycin is a predetermined and an amount calculated to achieve the desired effect, i.e., to effectively inhibit Trx1/TrxR redox system in an individual to whom the composition is administered.

The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., excipient, carrier, or vehicle.

Pentacyclic palmarumycins are structurally unique natural products with both antifungal and antibacterial activities, but their anti-neoplastic effects are not well established. Compounds such as auranofin, palmarumycin $CP_1$, 1,3-bis(2-chloroethyl)-1-nitrosourea, and AW464 have been shown to inhibit either thioredoxin, thioredoxin reductase, or both. Embodiments of the invention relate to analogues of the palmarumycin family. Further embodiments relate to the ability of the palmarumycin analogues to inhibit the thioredoxin-thioredoxin reductase (Trx-1/TrxR redox) system. These analogues are tested for their ability to inhibit tumor growth in vivo with and their use as a therapeutic agent. Additionally, embodiments provide use of palmarumycin analogues that inhibit Trx1/TrxR redox system to be used as lead compounds for the development of other therapeutic agents.

Methods for the inhibition of Trx1/TrxR redox system are also contemplated. Inhibition of Trx1/TrxR redox system may lead to inhibition of tumor growth, with the subsequent development of therapeutic agents. Inhibition of Trx/TrxR redox system may also lead to inhibition of cellular transcription factors, providing therapeutic compounds, or lead compounds for the discovery of therapeutic compounds, for the treatment of medical conditions such as diabetic neuropathy, Sjogren's syndrome, HIV-AIDS, rheumatoid arthritis, reperfusion injury or uncontrolled proliferation, as exemplified by cancer.

Since its discovery in the early 1960s, the thioredoxin-thioredoxin reductase system has been the subject of intense pharmacological studies. The two redox active proteins have been isolated from many species, and their medical interest is based in part on their value as indicators of widespread diseases such as rheumatoid arthritis, AIDS, and cancer. The cytosolic 12 kDa thioredoxin-1 (Trx-1) is the major cellular protein disulfide reductase and its dithiol-disulfide active site cysteine pair (CXXC) serves as an electron donor for enzymes such as, but not limited to, ribonucleotide reductase, methionine sulfoxide reductase, and transcription factors including NF-κβ and the Ref-1-dependent AP-1. Therefore, thioredoxin-1 is important for cellular redox regulation, signaling, and regulation of protein function, as well as defense against oxidative stress and control of growth and apoptosis.

Thioredoxin-1 acts in concert with the glutathione-glutathione reductase system but with a rate of reaction orders of magnitude faster. Eukaryotic thioredoxin reductases (TrxR) are 112-130 kDa, selenium-dependent dimeric flavoproteins that also reduce substrates such as hydroperoxides or vitamin C. These reductases contain redox-active selenylsulfide-selenolthiol active sites and are inhibited by aurothioglucose and auranofin. NADPH serves as reducing agent of thioredoxin by thioredoxin reductase.

Pathophysiological effects of Trx-1/TrxR are indicated by Trx-1 overexpression in human tumors such as, but not limited to, lung, colorectal and cervical cancers and leukemia. Secreted Trx-1 stimulates cancer cell growth and decreases sensitivity to induced apoptosis. The Trx-1/TrxR system is therefore an important target for chemotherapeutic intervention. Although inhibitors of TrxR such as auranofin and nitrosoureas are quite effective, the search for new, more specific, and less toxic compounds is ongoing.

Embodiments of the invention provide new chemical compounds that inhibit the activity of the Trx-1/TrxR redox system. Such compounds may be useful as therapeutic agents, pharmacological probes, and/or lead compounds for the development of therapeutic agents. These compounds may include inhibitors of the thioredoxin-thioredoxin reductase system which are less toxic than currently available Trx-1/TrxR redox inhibiting compounds.

In one embodiments of the present invention, a compound, or salt thereof, having the general formula:

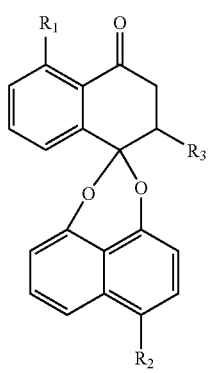

wherein $R_1$ may be H or OH;
$R_2$ may be OH, $OCH_3$, $O(CH_2)nCH_3$, $OCH(CH_3)CH_2nCH_3$, wherein n is 1-4, $OCH_2CH_2$-morpholino, $OC(O)CH_2NH_2$, $OC(O)CH(CH_3)NH_2$, $OC(O)CH(CH(CH_3)_2)NH_2$, $OC(O)CH(CH_2Phenyl)NH_2$, $OC(O)CH(CH_2$ p-OHPhenyl)$NH_2$,

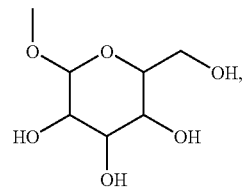

$OC(O)CH(CH_2OH)NH_2$, $OC(O)CH(CH_2SH)NH_2$, $OC(O)CH(CH_2COOH)NH_2$, $OC(O)CH(CH_2CH_2COOH)NH_2$, $OC(O)CH(CH_2CONH_2)NH_2$, $OC(O)CH(CH_2CH_2CONH_2)NH_2$, $OC(O)CH(CH(CH_3)CH_2CH_3)NH_2$, $OC(O)CH(CH_2CH(CH_3)_2)NH_2$, or $OC(O)CH(CH(OH)CH_3)NH_2$;

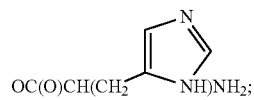

and $R_3$ may be a hydrogen, $NHNHC(CH_3)_2CONH_2$ or a carbon-carbon bond, with the proviso that if $R_1$ is OH and $R_3$ is a carbon-carbon bond, $R_2$ is not OH; or salts thereof is provided. Exemplary salts include, but are not limited to HCl, TFA, tosylate or any other pharmaceutically acceptable salt. Such compounds may be useful as therapeutic agents or pharmaceutical compositions that optionally contain a pharmaceutical excipient or carrier.

In an alternative embodiment provided is a compound having the following structure:

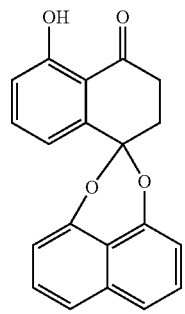

Palmarumycin CPl.

In another alternative embodiment provided is a compound having the following structure:
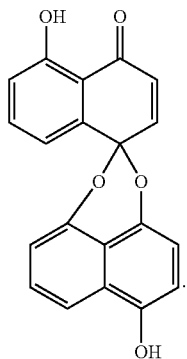
PX-960
Preferred embodiments relate to a compound of the structure:
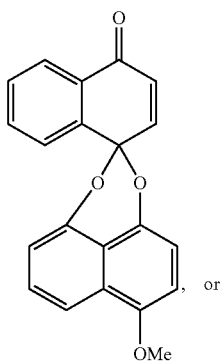
(PX-911)
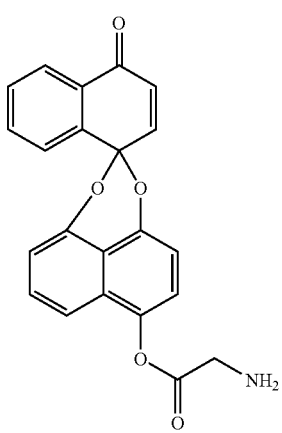
or salts thereof.
In a preferred embodiment, a salt of a palmarumycin compound has the structure:
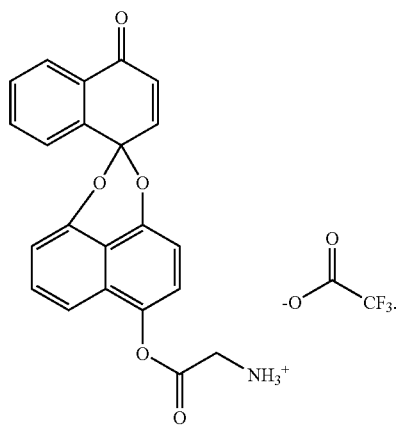
Other embodiments include compounds of the structures:
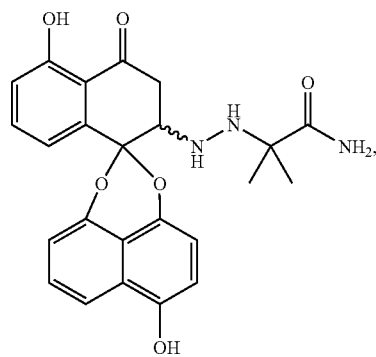
eee269-II
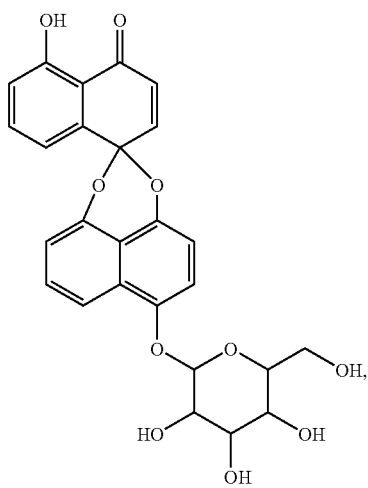
eee86-III

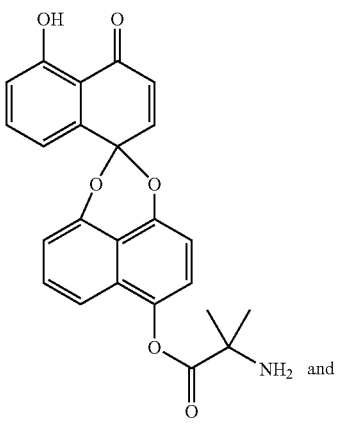

and

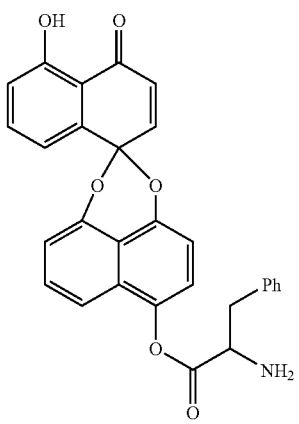

or salts thereof.

Preferred salts of the foregoing compounds include the following:

eee263-II

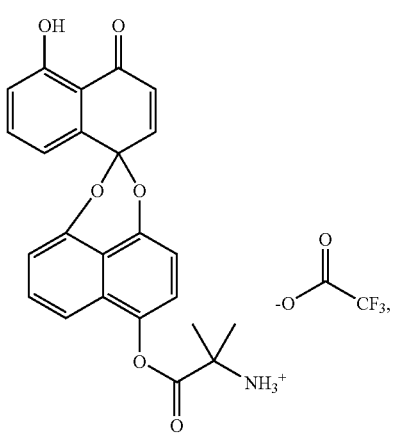

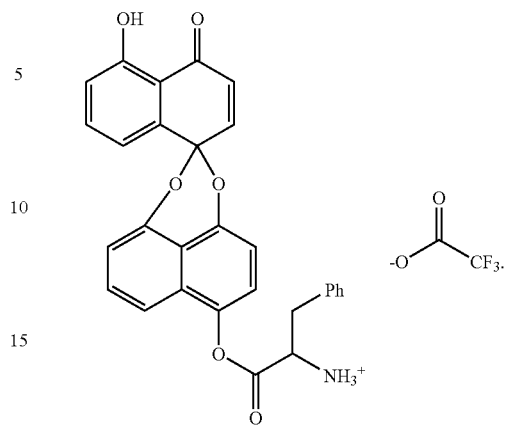

eee273-II

Each of the foregoing compounds may be useful as therapeutic agents, pharmaceutical compositions or diagnostic agents.

Another embodiment of the present invention provides a method of inhibiting a thioredoxin/thioredoxin reductase system comprising administering an effective amount of a palmarumycin analog having the general formula:

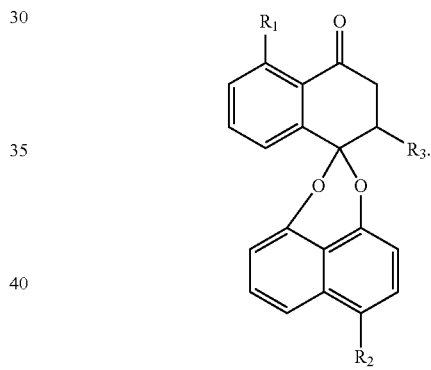

wherein $R_1$ may be H or OH;

$R_2$ may be OH, $OCH_3$, $O(CH_2)nCH_3$, $OCH(CH_3)CH_2nCH_3$, wherein n is 1-4, $OCH_2CH_2$-morpholino, $OC(O)CH_2NH_2$, $OC(O)CH(CH_3)NH_2$, $OC(O)CH(CH(CH_3)_2)NH_2$, $OC(O)CH(CH_2Phenyl)NH_2$, $OC(O)CH(CH_2$ p-OHPhenyl)$NH_2$

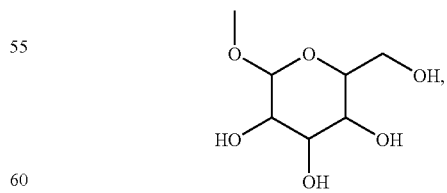

$OC(O)CH(CH_2OH)NH_2$, $OC(O)CH(CH_2SH)NH_2$, $OC(O)CH(CH_2COOH)NH_2$, $OC(O)CH(CH_2CH_2COOH)NH_2$, $OC(O)CH(CH_2CONH_2)NH_2$, $OC(O)CH(CH_2CH_2CONH_2)NH_2$, $OC(O)CH(CH(CH_3)CH_2CH_3)NH_2$, $OC(O)CH(CH_2CH(CH_3)_2)NH_2$, or $OC(O)CH(CH(OH)CH_3)NH_2$;

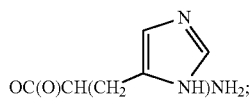

and

R$_3$ may be a hydrogen, NHNHC(CH$_3$)$_2$CONH$_2$ or a carbon-carbon bond, with the proviso that if R$_1$ is OH and R$_3$ is a carbon-carbon bond, R$_2$ is not OH; or salts thereof. Exemplary salts include, but are not limited to HCl, TFA, tosylate or any other pharmaceutically acceptable salt.

In another embodiment, methods of inhibiting thioredoxin reductase-1 by administering a palmarumycin analog described herein is provided. In another embodiment, such compounds may be useful in methods of treating diseases associated with the overexpression of thioredoxin-1, including, but not limited to, cancer, increased cell proliferation, and apoptosis by administering a therapeutically effective amount of a palmarumycin analog as described herein.

The compounds may be administered in an effective amount to a subject in need of such treatment. As such, the compounds described herein may be useful for the treatment of cancer and other proliferative disorders. Administration of the compounds, in the form of a therapeutic agent, may be carried out using oral, enteral, parenteral or topical administration, including, for example, intravenous, oral, transdermal or any other modes of administration optionally with a pharmaceutical excipient.

Pharmaceutical compositions can be used in the preparation of individual dosage forms. Consequently, pharmaceutical compositions and dosage forms of the invention may comprise the active ingredients disclosed herein (i.e., thioredoxin/thioredoxin reductase inhibitors, preferably palmarumycin analogs, more preferably a O-glycyl naphthoquinone spiroketal (PX-916)). Further embodiments of the invention may comprise any therapeutic compound and/or therapeutic regiment which is to be assessed for its efficacy in inhibiting a tumor. Pharmaceutical compositions and dosage forms of the invention can further comprise one or more excipients.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise an amount preferably in a range from about 0.05 mg/kg/day to about 5,000 mg/kg/day, more preferably in a range from about 0.5 mg/kg/day to about 500 mg/kg/day, more preferably in a range of about 1 mg/kg/day to about 50 mg/kg/day, and more preferably yet, the therapeutically effective amount is in a range from about 2 mg/kg/day to about 30 mg/kg/day.

The compounds of the invention are preferably administered in effective amounts. An effective amount is that amount of a preparation that alone, or together with further doses, produces the desired response. This may involve only slowing the progression of the disease temporarily, although preferably, it involves halting the progression of the disease permanently or delaying the onset of or preventing the disease or condition from occurring. This can be monitored by routine methods. Generally, doses of active compounds would be from about 0.01 mg/kg per day to 1000 mg/kg per day. It is expected that doses ranging from 20-500 mg/kg will be suitable, preferably intravenously, intramuscularly, or intradermally, and in one or several administrations per day.

In general, routine experimentation in clinical trials will determine specific ranges for optimal therapeutic effect for each therapeutic agent and each administrative protocol, and administration to specific patients will be adjusted to within effective and safe ranges depending on the patient condition and responsiveness to initial administrations. However, the ultimate administration protocol will be regulated according to the judgment of the attending clinician considering such factors as age, condition and size of the patient, the compound potencies, the duration of the treatment and the severity of the disease being treated. For example, a dosage regimen of the palmarumycin analogs, preferably an O-glycyl naphthoquinone spiroketal (PX-916), can be oral administration of from 1 mg/kg to 2000 mg/kg/day, preferably 1 to 1000 mg/kg/day, more preferably 50 to 600 mg/kg/day, in two to four (preferably two) divided doses, to reduce tumor growth. Intermittent therapy (e.g., one week out of three weeks or three out of four weeks) may also be used.

In the event that a response in a subject is insufficient at the initial doses applied, higher doses (or effectively higher doses by a different, more localized delivery route) may be employed to the extent that the patient tolerance permits. Multiple doses per day are contemplated to achieve appropriate systemic levels of compounds. Generally, a maximum dose is used, that is, the highest safe dose according to sound medical judgment. Those of ordinary skill in the art will understand, however, that a patient may insist upon a lower dose or tolerable dose for medical reasons, psychological reasons or for virtually any other reason.

The development of therapeutics typically begins with the identification of an active, or lead, compound that exhibits some of the properties required for safe and effective therapeutic intervention. Compounds with improved properties are subsequently derived through iterative cycles of analog preparation and testing. Lead compounds are often identified using high throughput screening (HTS), whereby large libraries containing about tens to thousands or more compounds are tested using relatively simple assays to measure inhibition of processes critical to the target indication, in this case inhibition of the Trx1/TrxR redox system. Typically this means using biochemical assays to measure the function of one or more macromolecular targets.

All lead compounds share a common property, in the present invention to inhibit the Trx1/TrxR redox system. Screening by assaying for the inhibition of the Trx1/TrxR redox system identifies a small subset of compounds which can be further studied. All compounds from the original library should be identified. Therefore, when multiple biochemical activities of the target (the Trx1/TrxR redox system) are known, all the activities of each compound can be measured separately without the prohibitive effort that may be needed to screen the entire library using multiple functional assays.

HTS permit screening of large numbers (i.e., tens to thousands or more) of compounds in an efficient manner. Automated and miniaturized HTS assays are particularly preferred. ITS assays are designed to identify "hits" or "lead compounds" having the desired inhibitory property, from which modifications can be designed to improve the desired property. Chemical modification of the "hit" or "lead compound" is often based on an identifiable structure/activity relationship between the "hit" and one or more of the palmarumycin analogues.

There are a number of different libraries used for the identification of specific small molecule inhibitors, including, (1) chemical libraries, (2) natural product libraries, and (3) combinatorial libraries comprised of random peptides, oligonucleotides or organic molecules.

Chemical libraries consist of structural analogs of known compounds or compounds that are identified as "hits" or "leads" via natural product screening. Natural product libraries are derived from collections of microorganisms, animals, plants, or marine organisms which are used to create mixtures for screening by: (1) fermentation and extraction of broths from soil, plant or marine microorganisms or (2) extraction of plants or marine organisms. Natural product libraries may include metabolites of a microorganism such as fungal metabolites, for example. Combinatorial libraries are composed of large numbers of peptides, oligonucleotides or organic compounds as a mixture. They are relatively easy to prepare by traditional automated synthesis methods.

Example 1

Various analogues of palmarumycin $CP_1$, were tested against two human breast cancer cell lines and several members displayed potent effects in inhibiting cell proliferation. A second generation series of palmarumycin $CP_1$ analogues showed increased in vitro activity, but failed to reduce tumor growth in vivo. This lack of correlation between enzyme and animal assays may be attributed to the low water solubility and limited bioavailability of the natural product lead structure (palmarumycin $CP_1$). Polar prodrug molecules with improved solubility and antitumor activity were then synthesized.

Typical solubilizing functions in prodrug derivatives include, but are not limited to, phosphonate or phosphate esters, amino acid esters, phenolic acetates, and various other acyl groups. Starting with the naphthoquinone spiroketal scaffold 5, (FIG. 1) the phenolic groups were used to introduce a charged, hydrolytically cleavable function. Coupling of compounds 5 and 6 (herein referred to as PX-960) with various Boc-protected amino acids proceeded in good yield and high regioselectivity (FIG. 1). Only the phenolic hydroxy group distal from the carbonyl functionality in 6 (PX-960) was acylated under the DCC mediated esterification conditions. This regioselectivity can be attributed to strong hydrogen bonding between the phenol and the carbonyl oxygen as well as the inductive attenuation of the nucleophilicity at this site. Following esterification, the carbamate was removed with 20% trifluoroacetate (TFA) in dichloromethane to afford a series of TFA salts which were tested for their ability to inhibit thioredoxin reductase along with general cytotoxicity.

Figure 2:
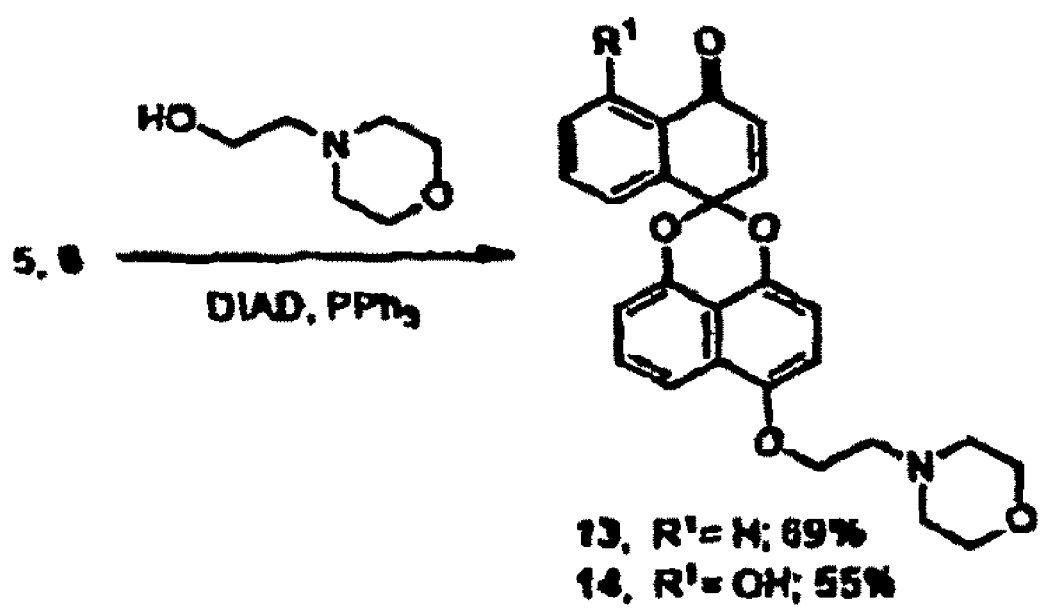
FIG. 2. Preparation of morpholine-derived prodrugs.

In addition to amino esters, the introduction of a tertiary amine in the form of a morpholine heterocycle was also investigated (FIG. 2). Once again, selective monoetherification was observed at the hydroxyl group distal from the carbonyl group. Compounds 13 and 14 (FIG. 2) were also subjected to biological evaluation.

As expected, all naphthoquinone spiroketal prodrugs 10-14 (FIG. 1-2) showed fundamentally equivalent low micromolar $IC_{50}$ values for MCF-7 cell growth inhibition compared to the parent phenol 6 (PX-960) (Table 1). In vitro inhibition of the thioredoxin-thioredoxin reductase system was more variable, and none of the prodrugs accomplished the nanomolar level of activity of PX-960, the parent compound, with glycyl prodrug 12 (herein referred to as PX-916) being the notable exception. Different amounts of the active drug may be released from the prodrug during the enzyme assays by spontaneous hydrolysis. However, prodrug PX-916 was considerably more water soluble (0.7 mg/mL vs <0.1 mg/mL for PX-960) than the parent active compound, and furthermore use of 20% β-cyclodextrin increased its solubility to 2 mg/mL. The half-life for the conversion of PX-916 to PX-960 in ethanol at room temperature was $t_{1/2}$>5 d. In water at room temperature and pH4, PX-916 had a $t_{1/2}$=37 h, but it was rapidly broken down at pH 7 and above ($t_{1/2}$<1 h). The relative lability of the prodrug at alkaline pH does not present a problem for formulation since pH 4 media can readily be administered to patients.

The chemical stability of PX-916 in mouse plasma at room temperature was $t_{1/2}$<2 minutes, and the prodrug was indeed converted to PX-960 according to HPLC analysis. Upon release from its O-acyl protective function, 6 (PX-960) had a $t_{1/2}$~31 min in plasma. Accordingly, glycine-derivative PX-916 met all the requirements that were set forth for further development as a lead compound in in vivo tumor xenograft models.

TABLE 1

IC$_{50}$ values [μM] for TrxR inhibition and human breast cancer cell growth inhibition.

| Entry | Compound | TrxR inhibitory activity | MCF-7 growth inhibition |
|---|---|---|---|
| 1 | 6 (PX-960) | 0.20 | 2.6 |
| 2 | 10 | 1.8 | 2.4 |
| 3 | 11 | 0.62 | 2.2 |
| 4 | 12 (PX-916) | 0.28 | 3.1 |
| 5 | 13 | 1.6 | 1.2 |
| 6 | 14 | 4.2 | 2.6 |

Because of the promising biological profile of prodrug PX 916, the enantiomers of the spirocycle PX-960 were resolved to test if they exhibited differential biological activities. The most direct approach would be a separation via chiral HPLC. The low solubility that plagued the biological testing of PX-960 limited the efforts towards chiral separation on a multi-milligram scale. However, small quantities (~1 mg) of enantiomerically pure PX-960 could be obtained with a Chiralcel AD-H column, and both enantiomers demonstrated comparable in vitro activity. Since the difference in the absolute configuration of PX-960 relates to the spatial orientation of the naphthaline ketal, the lack of enantioselectivity in the biological assay supports the hypothesis that this group is not primarily involved in any activity-determining interactions. Accordingly, the naphthaline ketal represents a preferred site for chemical changes that target the optimization of physicochemical properties.

The water soluble, reversible prodrug derivatives of potent inhibitors of the thioredoxin-thioredoxin reductase system were synthesized in a convergent fashion. The O-glycyl naphthoquinone spiroketal PX-916 demonstrated equivalent biological activity compared to the previous lead structure PX-960 in the in vivo MCF-7 tumor model as well as in the thioredoxin reductase inhibition assay. Moreover, PX-916 had 1-2 orders of magnitude improved aqueous solubility and, while stable at pH 4, rapidly released the active compound under physiological conditions.

General procedure for coupling reactions. To a partial suspension of spirocycle 6 (PX-960, 92 mg, 0.28 mmol) in CH$_2$Cl$_2$ (6 mL) was added N-(tert-butoxycarbonyl)glycine (58 mg, 0.33 mmol), DCC (74 mg, 0.36 mmol) and DMAP (7 mg, 0.06 mmol). The reaction mixture was stirred at room temperature for 1 h as the starting material gradually dissolved and a white precipitate was formed. The cloudy solution was filtered, rinsed with CH$_2$Cl$_2$ and concentrated under reduced pressure. The residue was purified by chromatography on SiO$_2$ (Hexanes/EtOAc, 7.3) to afford 112 mg (83%) of 4'-(N-tert-butoxycarbonylamino)acetic acid palmaruymycin CP$_1$, ester 9 as a yellow solid; Mp 182-185 (dec., EtOAc/Hexanes); IR 3375, 2980, 1772, 1662, 1609, 1506, 1419 cm$^{-1}$.

Spectral data for 9. $^1$H NMR (300 MHz, CHCl$_3$) δ 12.15 (s, 1H), 7.65 (t, 1H, J=8.0 Hz), 7.58-7.48 (m, 2H), 7.44 (d, 1H, J=7.5 Hz), 7.25 (d, 1H, J=8.4 Hz), 7.14 (d, 1H, 18.4 Hz), 7.03 (d, 1H, J=7.8 Hz), 7.01 (d, 1H, J=10.5 Hz), 6.95 (d, 1H J=8.2 Hz), 6.37 (d, 1H, J=10.5 Hz), 5.26 (brs, 1H), 4.34 (d, 2H, J 5.7 Hz), 1.50 (s, 9H): $^{13}$C NMR (75 MHz, CHCl$_3$) δ 188.8, 169.5, 162.1, 156.1, 147.6, 145.4, 141.1, 139.5, 138.8, 136.8, 130.2, 128.7, 127.4, 120.0, 119.9, 119.5, 115.8, 114.0, 113.7, 111.0, 109.6, 93.4, 80.6, 42.9. 28.6; MS (EI) m/z: (rel intensity) 416 ([M−OtBu]$^+$, 48), 389 (15), 332 (100); HRMS (EI) calcd for C$_{23}$H$_{14}$NO$_7$, (M−Ot−Bu) 416.0770, found 416.0776.

General procedure for deprotection. To a solution of glycine ester 9 (95 mg, 0.19 mmol) in CH$_2$Cl$_2$ (4 mL) was added trifluoroacetic acid (1 mL). The reaction mixture was stirred at room temperature for 30 min, and concentrated under reduced pressure to afford 98 mg (100%) of 12 as a yellow solid: IR 3200, 1772, 1665, 1610, 1420, 1205 cm$^{-1}$.

Spectral data for 12. $^1$H NMR (300 MHz, CD$_3$CN) δ 12.09 (brs, 1H), 7.70 (dd, 1H, J=8.4, 7.7 Hz), 7.64 (dd, 1H, J=8.6, 1.1 Hz), 7.58 (dd, 1H, J=8.5 Hz, 7.4 Hz), 7.45 (dd, 1H, J=7.7, 1.0 Hz), 7.33 (d, 1H, J=8.3 Hz), 7.14 (dd, 1H, J=8.4, 1.0 Hz), 7.07 (dd, 1H, J=7.3, 1.0 Hz), 7.06 (d, 1H, J=10.5 Hz), 7.00 (d, 1H, J=8.3 Hz), 6.35 (d, 1H, J=10.5 Hz), 4.30 (s, 2H); $^{13}$C-NMR (75 z, CD$_3$CN) δ 189.8, 167.4, 162.7, 160.8, (q, J=37.4 Hz), 148.5, 146.6, 141.5, 140.6, 139.7, 137.8, 130.9, 129.9, 128.0, 121.0, 120.6, 120.4, 117.1 (q, J=287.6 Hz), 116.4, 114.7, 114.4, 111.9, 110.4, 94.4, 41.8; MS (ESI) m/z (rel intensity) 390 ([M−OCOCF$_3$]$^+$, 100) 359 (47); HRMS (ESI) calcd for C$_{22}$H$_{16}$NO$_6$ (M−OCOCF$_3$) 390.0978, found 390.0975.

General procedure for attachment of morpholine tether. To a solution of spirocycle 6 (30 mg, 0.090 mmol) in THF (2 mL) was added N-(2-hydroxyethyl)morpholine (11 μL, 0.090 mmol), PPh$_3$, (26 mg, 0.10 mmol) and DIAD (20 μL, 0.10 mmol). The reaction mixture was stirred at room temperature for 3 h then concentrated under reduced pressure. The residue was purified by chromatography on SiO$_2$ (EtOAc/MeOH, 19:1) to afford 22 mg (55%) of 14 as a yellow solid film:

Spectral data for 14. $^1$H NMR (300 MHz, CHCl$_3$) δ 12.17 (s, 1H), 7.90 (d, 1H, J=8.5 Hz), 7.66 (t, 1H, J=8.0 Hz), 7.50-7.45 (m, 2H), 7.14 (dd, 1H, J=8.4, 0.9 Hz), 7.04 (d, 1H, J=7.3 Hz), 7.00 (d, 1H, J=10.5 Hz), 6.89 (d, 1H, J=8.3 Hz), 6.80 (d, 1H, J=8.3 Hz), 6.35 (d, 1H, J=10.5 Hz), 4.30 (t, 2H, J=5.5 Hz), 3.80-3.75 (m, 4H), 2.98 (t, 2H, J=5:5 Hz), 2.70-2.65 (m, 4H, J); MS (ESI), m/z (rel intensity) 446 ([M+1]$^+$, 100), 359 (65), 331 (20), 272 (12); HRMS (ESI) calcd for C$_{26}$H$_{24}$NO$_6$ (M+H) 446.1604, found 446.1581.

Spectral data for 10. $^1$H NMR (300 MHz, CD$_3$CN) δ 8.11 (dd, 1H, J=7.8, 1.1 Hz), 8.00 (dd, 1H, J=7.8, 0.9 Hz), 7.84 (td, 1H, J=7.6, 1.4 Hz), 7.71 (td, 1H, J=7.6, 1.2 Hz), 7.68-7.57 (m, 2H), 7.36 (d, 1H, J=8.3 Hz), 7.09 (dd, 1H, J=7.3, 1.0 Hz), 7.08 (d, 1H, J=10.6 Hz), 7.02 (d, 1H, J=8.3 Hz), 6.38 (d, 1H, J=10.6 Hz), 4.28 (s, 2H); MS (ESI) m/z (rel intensity) 374 ([M−OCOCF$_3$]$^+$, 37), 317 (100), 299 (30); HRMS (ESI) calcd for C$_{22}$H$_{16}$NO$_5$ (M−OCOCF$_3$) 374.1028, found 374.1034.

Spectral data for 11. $^1$H NMR (300 MHz, CD$_3$CN) δ 8.09 (dd, 1H, J=7.8, 1.3 Hz), 7.96 (d, 0.5H, J=7.8 Hz), 7.94 (d, 0.5H, J=7.8 Hz), 7.79 (t, 1H, J=7.6 Hz), 7.69 (d, 1H, J=7.7 Hz), 7.64 (d, 1H, J$_{8.5}$ Hz), 7.55 (t, 1H, J=8.1 Hz), 7.33 (d, 1H, J=8.2 Hz), 7.06-7.00 (m, 2H), 6.97 (dd, 1H, J=8.2, 1.7 Hz), 6.33 (d, 0.5H, J=10.6 Hz), 6.31 (d, 0.5H, J=10.6 Hz), 4.44 (d, 1H, J=4.2 Hz), 2.65-2.59 (m, 1H), 1.22 (d, 6H, J=6.9 Hz); MS (ESI) m/z (rel intensity) 416 ([M−OCOCF$_3$]$^+$, 100), 307 (12), 225 (18), 199 (18); HRMS (ESI) calcd for C$_{25}$H$_{22}$NO$_5$ (M−OCOCF$_3$) 416.1498, found 416.1485.

Spectral Data for 13 $^1$H NMR (300 MHz, CHCl$_3$) δ 8.18 Hz (dd, 1H, J=7.8, 1.2 Hz), 7.98 (d, 1H, J=7.8 Hz), 7.90 (d, 1H, J=8.3 Hz), 7.77 (td, 1H, J=7.5, 1.3 Hz), 7.67 (td, 1H, J=7.5, 1.1 Hz), 7.48 (t, 1H, J=8.1 Hz), 7.03 (d, 1H, J=7.0 Hz), 7.01 (d, 1H, J=10.5 Hz), 6.89 (d, 1H, J=8.3 Hz), 6.80 (d, 1H, J=8.3 Hz), 6.39 (d, 1H, J=10.5 Hz), 4.30 (t, 2H, J=5.6 Hz), 3.80-3.75 (m, 4H), 2.97 (t, 2H, J=5.6 Hz), 2.70-2.65 (m, 4H); MS (ESI) m/z (rel intensity) 430 ([M+1]$^+$, 100), 343 (12), 279 (8); HRMS (ESI) calcd for C$_{26}$H$_{24}$NO$_5$ (M+H) 430.1654, found 430.1568.

Retention times for the two 6 (PX-960) enantiomers on an AD-H column in 14% i-PrOH/Hexanes were 8.27 min and 10.07 min, respectively.

Stability. PX-916 was stable as a stock solution in ethanol at room temperature with a half life of >5 days. However, in 0.1 M sodium phosphate buffer PX-916 showed pH dependent degradation with a half life at pH 4.0 of 37 hr, at pH 7.0 a half life of 1 hr and at pH 10.0 a half life of <1 hr. Therefore, for in vitro studies PX-916 was used as a stock solution in ethanol, and for in vivo studies made fresh in pH 4.0 buffer vehicle.

Inhibition of TR. PX-916 was a potent inhibitor of purified human TR with an $IC_{50}$ of 0.28 μM, which is similar to that of palmarumycin (Table 2). However, unlike palmarumycin which is almost insoluble in aqueous media, PX-916 is soluble with an apparent maximum solubility in water of around 10 mg. Based upon the observation that PX-916 was rapidly converted to PX-960 in aqueous solution, the ability of PX-960 to inhibit purified human TR was measured and found to be similar to that of PX-916 (Table 2). PX-916 was a selective inhibitor of human TR compared to two other NADPH dependent reductases with a selectivity of at least 200 for human glutathione reductase and human cytochrome P450 reductase (Table 3).

TABLE 2

Inhibition of thioredoxin reductase and cell growth by palmuramycin analogs

| Compound | Inhibition of human thioredoxin reductase $IC_{50}$ (μM) | Inhibition of MCF-7 breast cancer cell growth $IC_{50}$ (μM) |
|---|---|---|
| palmarumycin C1 | 0.35 | 1.0 |
| PX-911 | 3.2 | 9.2 |
| PX-916 | 0.28 | 3.1 |
| PX-960 | 0.27 | 4.1 |

TABLE 3

Selectivity of PX-916 for TR compared to other human reductases

| human reductase (source) | Inhibition $IC_{50}$ (μM) | Selectivity |
|---|---|---|
| thioredoxin reductase (placenta) | 0.28 | |
| glutathione reductase (red blood cell) | >50 | >200 |
| cytochrome P-450 reductase (recombinant) | 29.2 | 104 |

Figure 3:
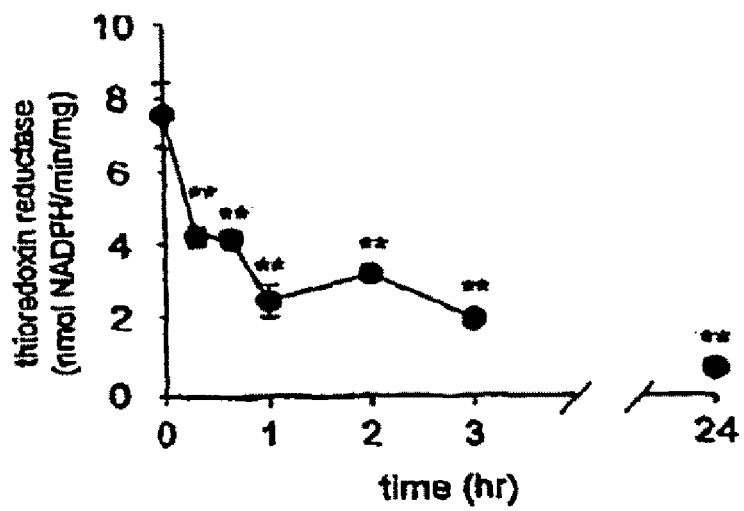
FIG. 3. Inhibition of cellular thioredoxin reductase by PX-916. MCF-7 human breast cancer cells grown in medium containing 1 μM Se for 7 days were treated with PX-916 and total cellular thioredoxin reductase activity measured. A. Time course of the inhibition of the thioredoxin reductase on exposure to 1 μM PX-916. B. Concentration dependence of the inhibition of thioredoxin reductase on exposure to various concentrations of PX-916 for 17 hours. In both cases values are the mean of 3 separate determinations and bars are SE. $P \leq 0.04$ or $p \leq 0.01$. C. Inhibition of MCF-7 tumor thioredoxin reductase by PX-916. MCF-7 human breast cancer xenografts were grown in female scid mice implanted with 17-β-estradiol 60 day slow-release pellets until they were ~300 mm³. The mice were administered a single dose of PX-916 of 25 mg/kg i.v. and tumors harvested at various times. Thioredoxin reductase activity was measured in tumor homogenates. Values are the mean of 3 mice at each time point and bars are SE. $p<0.01$ compared to pretreatment value.
Figure 3:
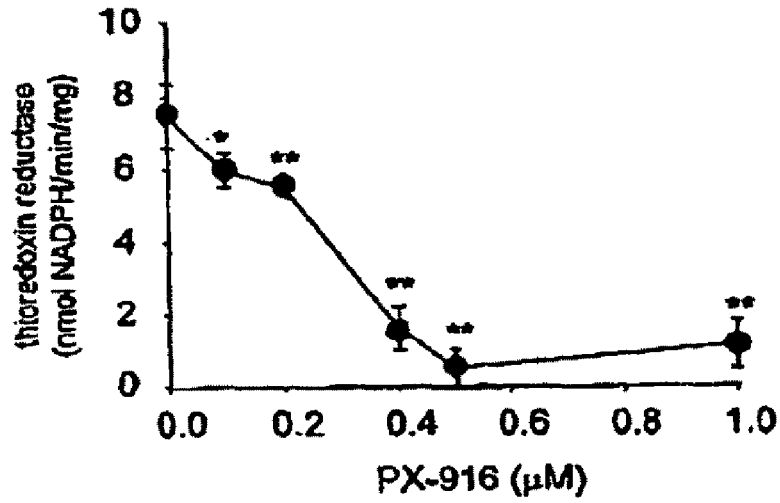
Figure 3:
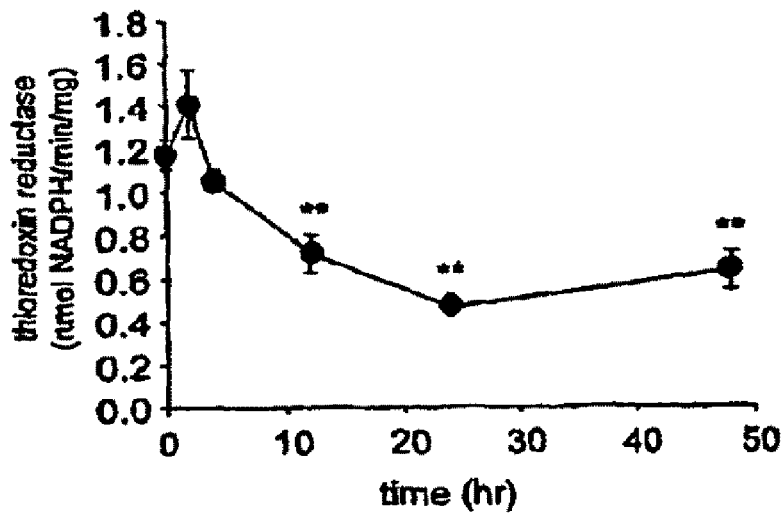

In vitro activity. Cell growth inhibition of MCF-7 human breast cancer cells by palmarumycin, PX-916 and PX-960 occurred at similar concentration of 1 to 3 μM (Table 2). MCF-7 human breast cancer cells were grown in medium containing 1 μM selenium (Se) for 7 days which increased cellular thioredoxin reductase activity by about 5 fold as previously reported. When the cells were exposed to 1 μM PX-916 there was a time dependent inhibition of cellular TR that was maximum at 24 hr (FIG. 3A). The $IC_{50}$ for inhibition of cellular TR by PX-916 was 0.25 μM and maximum inhibition occurred at 0.5 μM (FIG. 3B). Thus, inhibition of purified human TR, MCF-7 cellular TR and cell growth inhibition of MCF-7 cells by PX-916 occurred at about the same concentrations.

Figure 4:
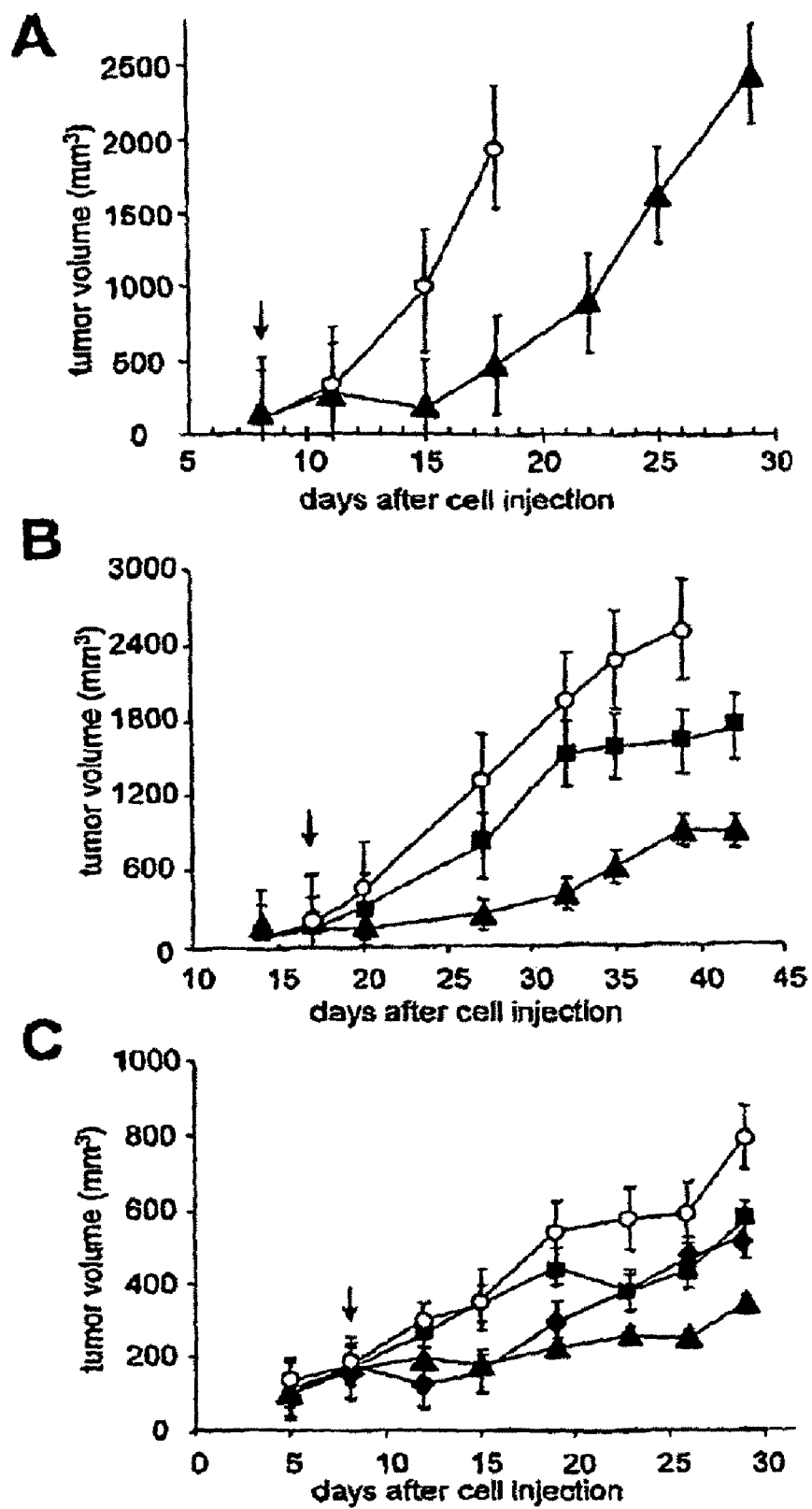
FIG. 4. Antitumor activity of PX-916. A. Female beige nude mice were inoculated subcutaneously (s.c.) with $10^7$ A-673 rhabdomyosarcoma cells. When tumors were 100 mm³ on day 8 (arrow) dosing was begun with (○) vehicle alone; (▲) PX-916 10 mg/kg intraperitoneally (i.p.) daily for 4 doses. B. Female scid mice were inoculated s.c. with $10^7$ SHP-77 human small cell lung cancer cells. When tumors were 130 mm³ on day 17 (arrow) dosing was begun with (○) vehicle alone; (■) PX-916 10 mg/kg i.v. daily for 8 doses; (Α) PX-916 25 mg/kg i.v. daily for 5 doses. C. Female scid mice implanted 1 day previously with a 17-β-estradiol 60 day slow release pellet were inoculated s.c. with 107 MCF-7 human breast cancer cells. When tumors were 180 mm³ on day 8 (arrow) dosing was begun with (○) vehicle alone; (◊) PX-916 27.5 mg/kg i.v. daily for 5 doses. In both A and B values are the mean of 8 mice per group and bars are SE.

In vivo inhibition of tumor TR and antitumor activity. A single intravenous (i.v.) dose of PX-916 of 25 mg/kg inhibited MCF-7 human tumor xenograft TR up to about 60% at 24 hr and the inhibition was maintained for at least 48 hr (FIG. 3C). The growth of A-673 human rhabdomyosarcoma xenografts (±SE, n=6 mice) was decreased from 153±35 mm$^3$/d in the vehicle control to 5±3 mm$^3$/d for 5 days after dosing with PX-916 at 30 mg/kg/d ip for five doses (97% inhibition; P>0.01) (FIG. 4A). PX-916 administered i.v. showed good antitumor activity against the SHP-77 small cell lung cancer with a decrease in tumor growth rate 5 days after the end of dosing (±SE, n=8 mice) from about 150±48 mm$^3$/day in vehicle control to 27 mm$^3$/day when administered at 25 mg/kg i.v. daily for 5 doses (82% inhibition; P<0.05) (FIG. 4B). In this study 3 of eight nice had no histologically detectable tumor when the study was terminated on day 42. Tumor growth was decreased to about 91±24 mm$^3$/day (39% inhibition, P<0.05) by PX-916 administered i.v. at 10 mg/kg i.v. daily for 8 doses. The growth of MCF-7 human breast cancer xenografts was, decreased 5 days after the end of dosing from 47+10 mm$^3$/day in the vehicle control to 22±4 mm$^3$/day by PX-916 at 27.5 mg/kg i.v. daily for 5 doses (52% inhibition, P<0.05), 22±8 mm$^3$/day by PX-916 at 27.5 mg/kg i.v every other day for 5 doses (52% inhibition, P>0.05) and to 18.5±8 mm$^3$/day by PX-916 at 27.5 mg/kg orally for 5 doses (62% inhibition, P<0.05) (FIG. 4C).

Figure 5:
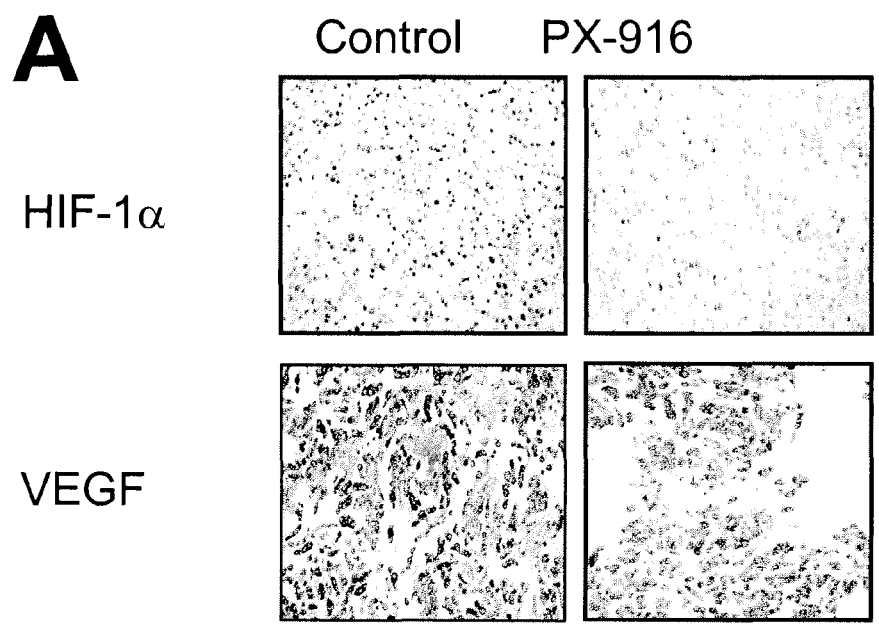
FIG. 5. Inhibition of tumor HIF-1α, VEGF and thioredoxin reductase by repeated administration of PX-916. Female scid mice were implanted 1 d previously with a 90-d 17β-estradiol slow release pellet were inoculated s.c. with $10^7$ MCF-7 human breast cancer cells. When the tumors were 300 mm³, vehicle or 25 mg/kg/d PX-916 was given i.v. for five doses. Twenty four hours later, the tumors were removed and stained by immunohistochemistry for HIF-1α and VEGF (A) or assayed for thioredoxin reductase activity (B). Columns mean of four mice, SE. P<0.05.
Figure 5:
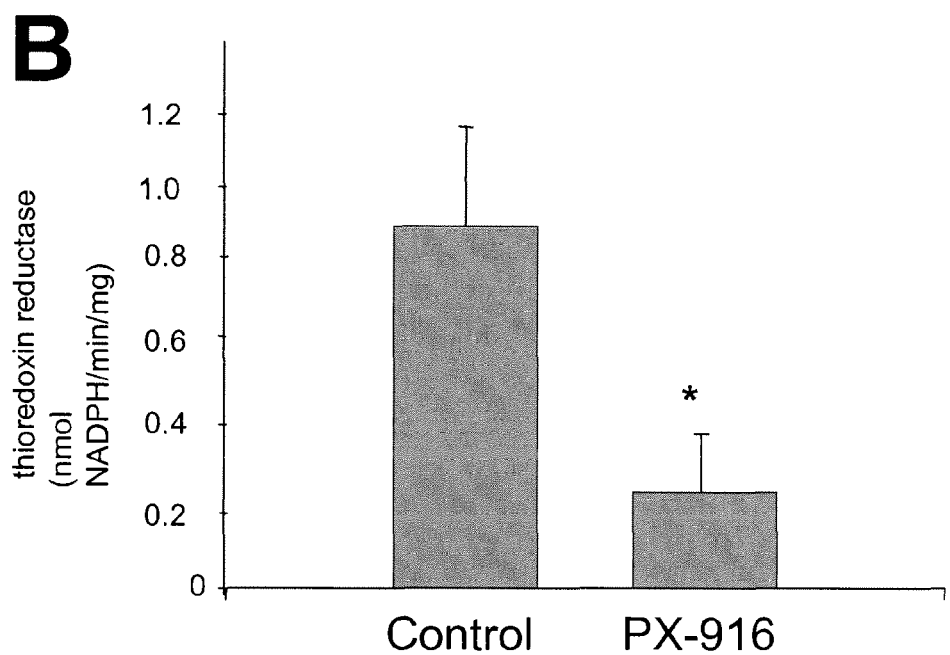

Tumor HIF-1α and VEGF. Levels of the HIF-1α transcription factor and its downstream target VEGF are increased by thioredoxin-1 expression. We examined the effect of PX-916 administration on tumor HIF-1α and VEGF levels (FIG. 5A). Twenty-four hours after the last dose of five daily doses of PX-916 of 25 mg/kg, there was a decrease in MCF-7 xenograft staining for both HIF-1α and VEGF. At the same time, levels of tumor thioredoxin reductase activity were decreased by 75% (FIG. 5B).

Toxicity. A single i.v. dose of PX-916 of 50 mg/kg to female scid mice was lethal. However, female scid mice tolerated 5 daily doses of PX-916 of 25 mg/kg i.v. The major toxicities observed 24 hr after the last dose was neutropenia and thrombocytopenia, with no observable increase in plasma liver-enzymes and no significant weight loss (Table 4).

TABLE 4

Toxicity of PX-916 in scid mice. PX-916 was administered to female scid mice at 25 mg/kg iv daily for 5 days and mice were killed 24 hr after the last dose. There were 4 mice per group and values are the mean ± SE.

| Schedule | Dose | Δbodywtg | ALT U/I | AST U/I | WB K/μl | NE K/μl | LY K/μl | MO K/μl | RBC M/μl | Hb g/dl | PLT K/μl |
|---|---|---|---|---|---|---|---|---|---|---|---|
| Control | | −1.2 ±1.5 | 30.3 ±10 | 154.1 ±62.4 | 3.0 ±0.6 | 2.5 ±0.5 | 0.4 ±0.1 | 0.11 ±0.05 | 9.4 ±0.5 | 15.5 ±0.7 | 773 ±67 |
| QD × 5 iv | 25 | −0.6 ±0.3 | 39.8 ±12.8 | 166.9 ±29.8 | 1.3 ±0.6* | 0.9 ±0.3* | 0.3 ±0.1 | 005 ±0.01 | 8.9 ±0.4 | 14.9 ±0.4 | 436 ±142* |

*= p < 0.05

Pharmacokinetics. When incubated with fresh mouse plasma at room temperature, PX-960 had a half life of about 31 minutes at room temperature while PX-916 rapidly disappeared and was converted to PX-960 with a half life of less than 2.0 minutes. When PX-916 was administered to mice at 25 mg/g i.v., it could not be detected in plasma 5 minutes after administration and only a very small peak of the parent compound PX-960 could be detected at 5 minutes. No PX-960 was detected at 30 minutes. Two metabolite peaks could be seen at 5 minutes, but were undetectable by 30 minutes.

PX-916 was synthesized as a water soluble prodrug of the palmarumycin analog PX-960 and was found to retain the ability to inhibit purified TrxR with an $IC_{50}$ of 0.28 µM. PX-916 also inhibited TrxR activity in MCF-7 human breast cancer cells with an $IC_{50}$ of 0.25 µM and was an inhibitor of MCF-7 cell growth with an $IC_{50}$ of 3.1 µM. PX-916 was an NADPH and time dependent, apparently, irreversible inhibitor of thioredoxin reductase-1, most likely reacting with the selenocysteine-containing catalytic site. Two other NADPH dependent reductases, human glutathione reductase and cytochrome P-450 reductase, were not inhibited by PX-916 until concentrations were increased to greater than 100 fold higher.

Stability studies showed that at physiological pH PX-916 was stable for about 1 hr and slowly converted to its parent PX-960 with a half life of 1 hr. It was much more stable at pH 4.0 and was formulated at this pH for i.v. administration. In mouse plasma the breakdown of PX-916 to PX-960 was rapid with a half life less than 2 minutes. Thus, the inhibition of TrxR in tumor xenografts and the antitumor activity is likely to be almost completely due to the parent PX-960. PX-960 could be detected only transiently in mouse plasma after administration of PX-916 due to rapid metabolism or likely rapid distribution of the very lipophilic PX-960. Thus, PX-916 provides a novel soluble and stable prodrug for the administration of PX-960.

When a single dose of 25 mg/kg was administered to mice with MCF-7 breast cancer xenografts the tumor TrxR activity was inhibited by up to 60% and remained inhibited for 48 hr. Repeated administration of PX-916 for five (5) days gave 75% inhibition of tumor thioredoxin reductase 24 hrs after the last dose.

PX-916 given i.p. or i.v. showed antitumor activity against A673 rhabdomyosarcoma, SHP-77 small cell lung cancer, and MCF-7 breast cancer. In SHP-77, complete tumor regressions were seen in some mice. The most active schedule was every other day administration, and tumor growth was inhibited as long as the drug was given. Significant antitumor activity was not seen following oral administration at doses that gave i.v. antitumor activity. Thioredoxin-1 acts by a redox mechanism to increase HIF-1α levels and VEGF formation, associated with an increase in tumor angiogenesis, and this effect was reversed by a thioredoxin-1 inhibitor. MCF-7 tumor xenografts in mice treated with PX-916 showed a decrease in tumor HIF-1α and VEGF presumably due to the inhibition of thioredoxin-1 redox signaling. Inhibition of thioredoxin reductase-1 might affect other pathways in the cell. A recent study using small interfering RNA to knockdown thioredoxin reductase-1 expression and microarray analysis showed changes in leukotriene B4 12-hydroxydehydrogenase, ubiquitin D, differentiation enhancing factor, fibronectin 1, apolipoprotein 3, prosaposin, choline/ethanolamine phosphotransferase, and IFN-a-inducible protein genes.

PX-916, a water-soluble prodrug of a palmarumycin CP1 analogue, rapidly releases the parent compound at physiologic pH and in plasma, but is stable at acid pH, allowing its i.v. administration. PX-916 is an inhibitor of purified human thioredoxin reductase-1 and of thioredoxin reductase activity in cells and tumor xenografts when given to mice. PX-916 exhibited antitumor activity against several animal tumor models, with some cures, and blocked the expression of the downstream targets of thioredoxin-1 signaling, HIF-1α and VEGF, in the tumors.

Example 2

Further palmarumycin analogs were synthesized and tested. The following analogs were synthesized: eee269-II, eee86-M, eee263-11 and eee273-II. The stability of the analogs was measured in various solutions. The stability of 100 g/ml of compound in a 0.1 M sodium phosphate buffer is presented in Table 5 below.

TABLE 5

| Compound | pH | $T_{1/2}$ |
|---|---|---|
| eee269-11 | 7.0 | 12 min |
|  | 4.0 | >100 hr |
| eee86-111 | 7.0 | >100 hr |
|  | 4.0 | >100 hr |
| eee262-11 | 7.0 | >100 hr |
|  | 4.0 | >100 hr |
| eee273-11 | 7.0 | >100 hr |
|  | 4.0 | >100 hr |

Figure 6:
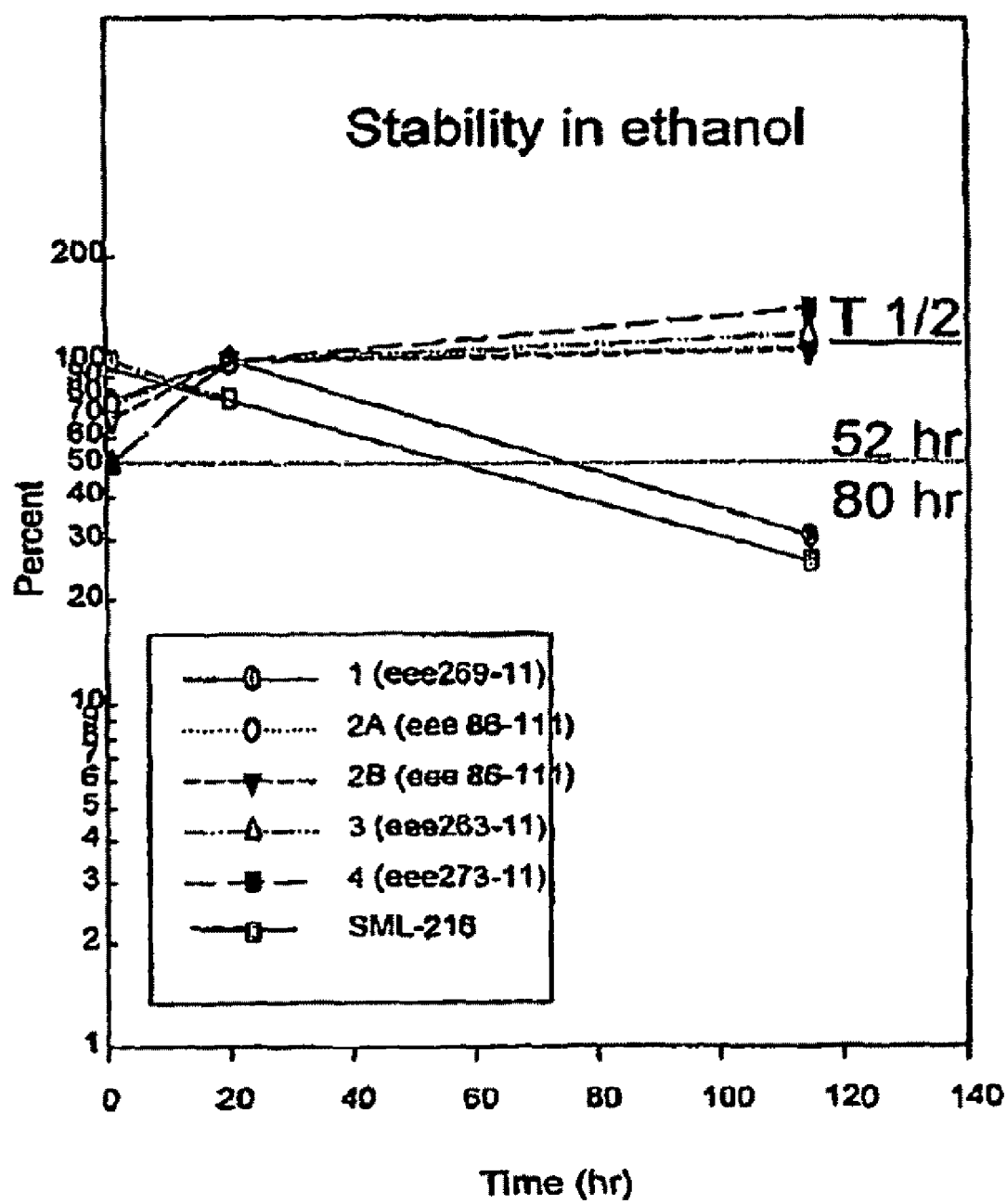
FIG. 6. Stability of palmarumycin analogs in ethanol. (●) 1 (eee269-111); (○) 2A (eee86-111); (▲) 2B (eee86-111); (Δ) 3 (eee-263-111); (■) 4 (eee-273-11); and (□) SML-216.

The stability of the analogs in ethanol is presented in FIG. 6. The stability of the analogs and formation of the parent compound in plasma was measured and is presented in FIG. 7, FIG. 8 and Table 6 (measured by the formation of parent compound over the first 20 min of incubation at 1 mg/ml and at 33° C.), below. As shown below, eee273-II appears very insoluble at 1 mg/ml, but not studied in mouse plasma and eee269-II was not studied in plasma because it is unstable in aqueous solutions.

TABLE 6

Stability of palmarumycin analog prodrugs in plasma.

| | Mouse Plasma area/20 min | ES1e mouse plasma area/20 min | Human plasma area/20 min |
|---|---|---|---|
| SML-216 | 350 | 210 | 135 |
| eee86-III | 20 | 17 | 70 |
| eee263-II | 42 | 82 | 81 |
| eee273-II | 19 | | |

Although the present invention has been described in considerable detail with reference to certain preferred embodiments thereof, other versions are possible. Therefore the spirit and scope of the appended claims should not be limited to the description and the preferred versions contained within this specification.

What is claimed is:

1. A compound, or salt thereof, having the general formula:

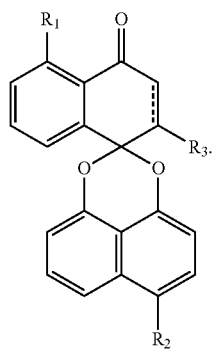

wherein

R₁ is H or OH;

R₂ is selected from the group consisting of O(CH₂)nCH₃, OCH(CH₃)CH₂nCH₃, OC(O)CH(CH₃)NH₂, OC(O)CH(CH₂Phenyl)NH₂, OC(O)CH(CH₂p-OHPhenyl)NH₂

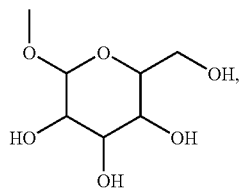

OC(O)CH(CH₂OH)NH₂, OC(O)CH(CH₂SH)NH₂, OC(O)CH(CH₂COOH)NH₂, OC(O)CH(CH₂CH₂COOH)NH₂, OC(O)CH(CH₂CONH₂)NH₂, OC(O)CH(CH₂CH₂CONH₂)NH₂, OC(O)CH(CH(CH₃)CH₂CH₃)NH₂, OC(O)CH(CH₂CH(CH₃)₂)NH₂, OC(O)CH(CH(OH)CH₃)NH₂; and

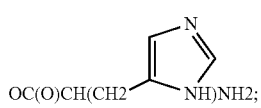

n is 1-4, and

R₃ is hydrogen, or NHNHC(CH₃)₂CONH₂, ┆ represents the option of having a double bond.

2. A method of inhibiting overexpression of thioredoxin-1 in a subject in need thereof comprising administering a therapeutically effective amount of

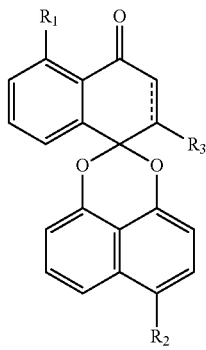

or a salt thereof, wherein

R₁ is H or OH;

R₂ is selected from the group consisting of O(CH₂)nCH₃, OCH(CH₃)CH₂nCH₃, OC(O)CH(CH₃)NH₂, OC(O)CH(CH₂Phenyl)NH₂, OC(O)CH(CH₂ p-OHPhenyl)NH₂

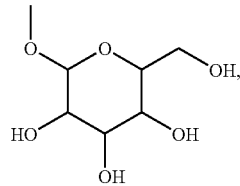

OC(O)CH(CH₂OH)NH₂, OC(O)CH(CH₂SH)NH₂, OC(O)CH(CH₂COOH)NH₂, OC(O)CH(CH₂CH₂COOH)NH₂, OC(O)CH(CH₂CONH₂)NH₂, OC(O)CH(CH₂CH₂CONH₂)NH₂, OC(O)CH(CH(CH₃)CH₂CH₃)NH₂, OC(O)CH(CH₂CH(CH₃)₂)NH₂, OC(O)CH(CH(OH)CH₃)NH₂, and

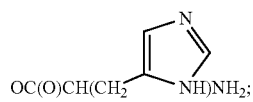

n is 1-4, and

R₃ is H, or NHNHC(CH₃)₂CONH₂, ┆ represents the option of having a double bond.

3. A method of treating cancer in a subject in need of treatment comprising administering a therapeutically effective amount of:

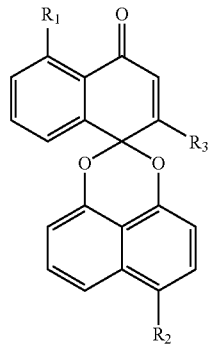

or a salt thereof, wherein
$R_1$ is H or OH;
$R_2$ is selected from the group consisting of $O(CH_2)nCH_3$, $OCH(CH_3)CH_2nCH_3$, $OC(O)CH(CH_3)NH_2$, $OC(O)CH(CH_2Phenyl)NH_2$, $OC(O)CH(CH_2$ p-OHPhenyl)$NH_2$

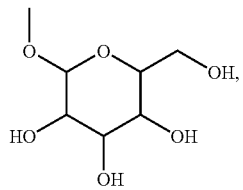

$OC(O)CH(CH_2OH)NH_2$, $OC(O)CH(CH_2SH)NH_2$, $OC(O)CH(CH_2COOH)NH_2$, $OC(O)CH(CH_2CH_2COOH)NH_2$, $OC(O)CH(CH_2CONH_2)NH_2$, $OC(O)CH(CH_2CH_2CONH_2)NH_2$, $OC(O)CH(CH(CH_3)CH_2CH_3)NH_2$, $OC(O)CH(CH_2CH(CH_3)_2)NH_2$, $OC(O)CH(CH(OH)CH_3)NH_2$, and $OC(O)CH(CH_2$

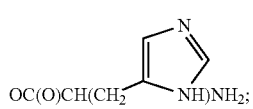

$NH_2$;
n is 1-4, and
$R_3$ is H, or $NHNHC(CH_3)_2CONH_2$; ┆ represents the option of having a double bond.

4. A method of inhibiting tumor growth in a subject in need of treatment comprising administering a therapeutically effective amount of:

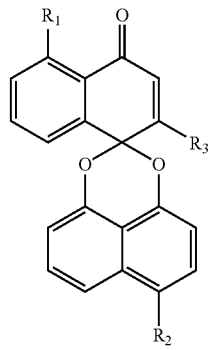

or a salt thereof, wherein
$R_1$ is H or OH;
$R_2$ is selected from the group consisting of $O(CH_2)nCH_3$, $OCH(CH_3)CH_2nCH_3$, $OC(O)CH(CH_3)NH_2$, $OC(O)CH(CH_2Phenyl)NH_2$, $OC(O)CH(CH_2$ p-OHPhenyl)$NH_2$

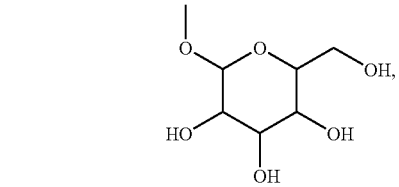

$OC(O)CH(CH_2OH)NH_2$, $OC(O)CH(CH_2SH)NH_2$, $OC(O)CH(CH_2COOH)NH_2$, $OC(O)CH(CH_2CH_2COOH)NH_2$, $OC(O)CH(CH_2CONH_2)NH_2$, $OC(O)CH(CH_2CH_2CONH_2)NH_2$, $OC(O)CH(CH(CH_3)CH_2CH_3)NH_2$, $OC(O)CH(CH_2CH(CH_3)_2)NH_2$, $OC(O)CH(CH(OH)CH_3)NH_2$, and

$NH_2$;
n is 1-4, and
$R_3$ is H, or $NHNHC(CH_3)_2CONH_2$; ┆ represents the option of having a double bond.

5. A compound, or salt thereof, having the general formula:

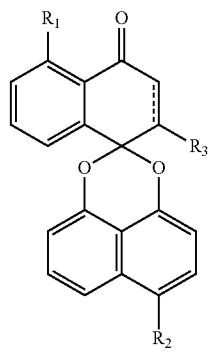

wherein $R_1$ is H or OH;
$R_2$ is selected from the group consisting of $OCH_2CH_2$-morpholino, $OC(O)CH_2NH_2$, and $OC(O)CH(CH(CH_3)_2)NH_2$;

and $R_3$ is hydrogen, ┊ represents the option of having a double bond.

6. The compound of claim 5, wherein said compound is:

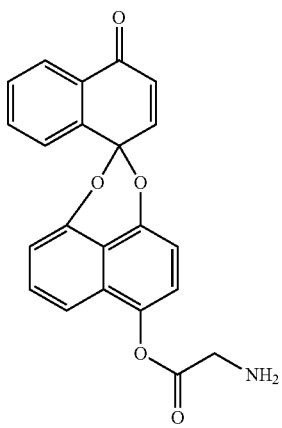

and salts thereof.

7. The compound of claim 5, wherein said compound is:

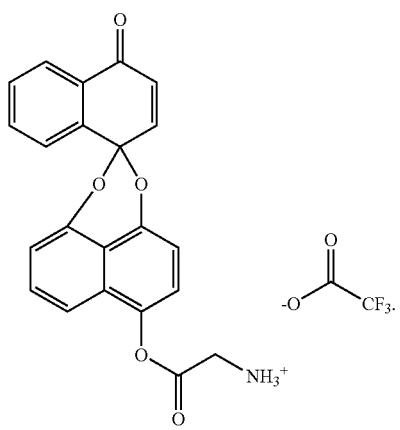

8. A method of inhibiting overexpression of thioredoxin-1 in a subject in need thereof comprising administering a therapeutically effective amount of

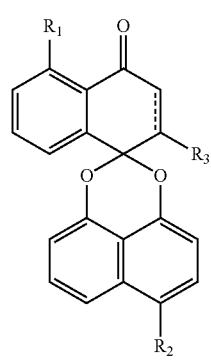

or a salt thereof, wherein $R_1$ is H or OH; $R_2$ is selected from the group consisting of $OCH_2CH_2$-morpholino, $OC(O)CH_2NH_2$, and $OC(O)CH(CH(CH_3)_2)NH_2$; and
$R_3$ is H, ┊ represents the option of having a double bond.

9. The method of claim 8, wherein said compound is:

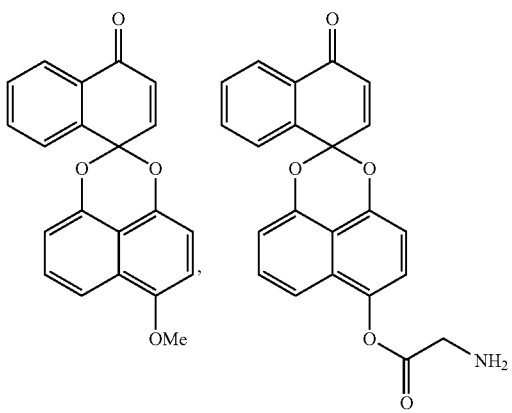

and salts thereof.

10. The method of claim 8, wherein said compound is:

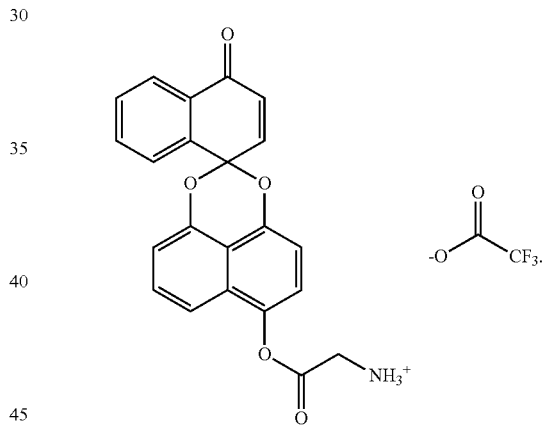

11. A method of treating cancer in a subject in need of treatment comprising administering a therapeutically effective amount of:

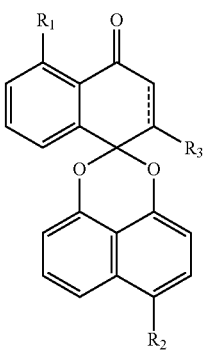

or a salt thereof, wherein $R_1$ is H or OH;

R$_2$ is selected from the group consisting of OCH$_2$CH$_2$-morpholino, OC(O)CH$_2$NH$_2$, and OC(O)CH(CH(CH$_3$)$_2$)NH$_2$; and R$_3$ is H; ┆ represents the option of having a double bond.

12. The method of claim 11, wherein said compound is:

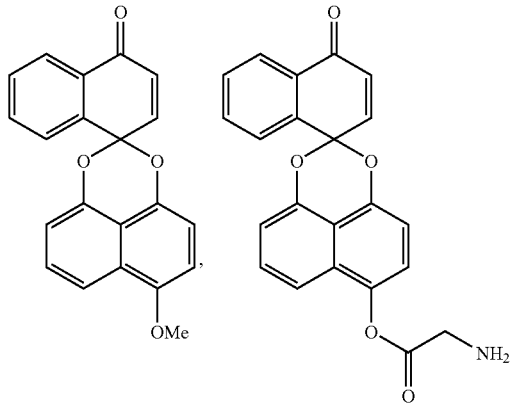

and salts thereof.

13. The method of claim 11, wherein said compound is:

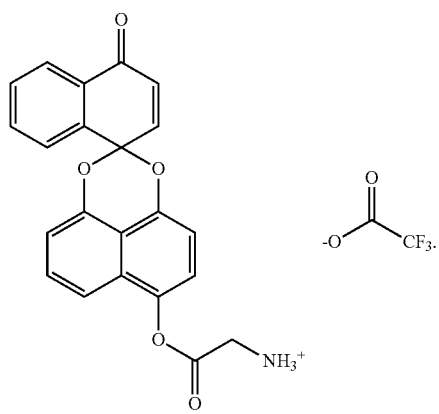

14. A method of inhibiting tumor growth in a subject in need of treatment comprising administering a therapeutically effective amount of:

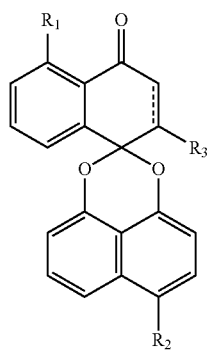

or a salt thereof, wherein

R$_1$ is H or OH;

R$_2$ is selected from the group consisting of OCH$_2$CH$_2$-morpholino, OC(O)CH$_2$NH$_2$, and OC(O)CH(CH(CH$_3$)$_2$)NH$_2$; and R$_3$ is H; ┆ represents the option of having a double bond.

15. The method of claim 14, wherein said compound is:

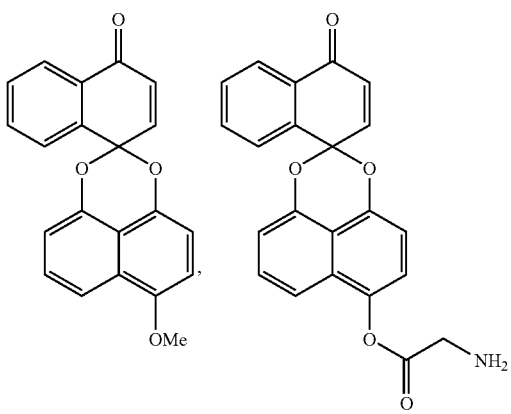

and salts thereof.

16. The method of claim 14, wherein said compound is:

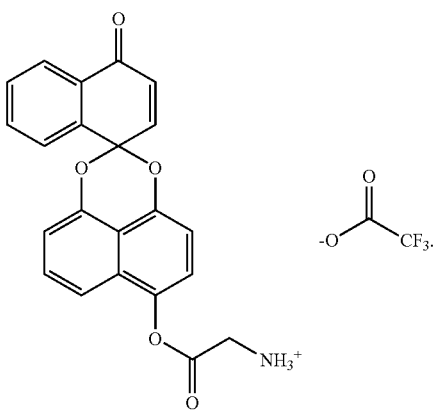

* * * * *